United States Patent
Trier et al.

(10) Patent No.: US 10,213,603 B2
(45) Date of Patent: Feb. 26, 2019

(54) ARBITRARY WAVEFORM GENERATOR AND NEURAL STIMULATION APPLICATION WITH SCALABLE WAVEFORM FEATURE AND CHARGE BALANCING

(71) Applicant: Nuvectra Corporation, Plano, TX (US)

(72) Inventors: Stephen C. Trier, Mayfield Heights, OH (US); Jeffrey A. Weisgarber, Jewett, OH (US); Richard J. Polefko, Parma, OH (US)

(73) Assignee: NUVECTRA CORPORATION, Plano, TX (US)

( * ) Notice: Subject to any disclaimer, the term of this patent is extended or adjusted under 35 U.S.C. 154(b) by 0 days.

(21) Appl. No.: 15/584,867

(22) Filed: May 2, 2017

(65) Prior Publication Data
US 2017/0232258 A1    Aug. 17, 2017

Related U.S. Application Data

(60) Division of application No. 13/828,102, filed on Mar. 14, 2013, now Pat. No. 9,656,076, which is a continuation-in-part of application No. 13/081,896, filed on Apr. 7, 2011, now Pat. No. 8,996,115, and a continuation-in-part of application No. 13/082,097, filed on Apr. 7, 2011, now Pat. No. 8,996,117, and a continuation-in-part of application No. 13/081,936, filed on Apr. 7, 2011, now Pat. No. 8,874,219.

(51) Int. Cl.
*A61N 1/00*    (2006.01)
*A61N 1/36*    (2006.01)

(52) U.S. Cl.
CPC ..... *A61N 1/36071* (2013.01); *A61N 1/36125* (2013.01); *A61N 1/36146* (2013.01); *A61N 1/36128* (2013.01)

(58) Field of Classification Search
CPC ............ A61N 1/36071; A61N 1/36146; A61N 1/3605
USPC .......................................... 607/46
See application file for complete search history.

(56) References Cited

U.S. PATENT DOCUMENTS

| | | |
|---|---|---|
| 4,898,173 A | 2/1990 | Daglow et al. |
| 5,417,714 A | 5/1995 | Levine et al. |
| 5,690,688 A | 11/1997 | Noren et al. |

(Continued)

FOREIGN PATENT DOCUMENTS

| | | |
|---|---|---|
| DE | 10134277 | 1/2003 |
| EP | 1995685 | 11/2008 |

(Continued)

OTHER PUBLICATIONS

European Application No. 13186926.5, Extended European Search Report dated Jan. 8, 2014, 7 pgs.

(Continued)

*Primary Examiner* — Amanda Hulbert
*Assistant Examiner* — Philip C Edwards
(74) *Attorney, Agent, or Firm* — Haynes and Boone, LLP; Eric Li

(57) ABSTRACT

A method, device and/or system for generating arbitrary waveforms of a desired shape that can be used for generating a stimulation pulse for medical purposes such as for spinal cord stimulation therapy, including the option of using such arbitrary waveforms for charge balancing purposes.

20 Claims, 10 Drawing Sheets

(56) References Cited

U.S. PATENT DOCUMENTS

| | | |
|---|---|---|
| 5,730,628 A | 3/1998 | Hawkins |
| 5,865,641 A | 2/1999 | Swart et al. |
| 6,029,090 A | 2/2000 | Herbst |
| 6,058,326 A | 5/2000 | Hess et al. |
| 6,120,467 A | 9/2000 | Schallhorn |
| 6,219,580 B1 | 4/2001 | Faltys et al. |
| 6,289,247 B1 | 9/2001 | Faltys et al. |
| 6,393,316 B1 | 5/2002 | Gillberg et al. |
| 6,505,077 B1 | 1/2003 | Kast et al. |
| 6,622,048 B1 | 9/2003 | Mann et al. |
| 6,625,488 B2 | 9/2003 | Poore et al. |
| 6,659,968 B1 | 12/2003 | McClure |
| 6,687,538 B1 | 2/2004 | Hrdlicka et al. |
| 6,728,578 B1 | 4/2004 | Voelkel et al. |
| 6,754,533 B1 | 6/2004 | Helfinstine et al. |
| 6,892,098 B2 | 5/2005 | Ayal et al. |
| 7,065,412 B2 | 6/2006 | Swoyer et al. |
| 7,177,691 B2 | 2/2007 | Meadows et al. |
| 7,187,976 B2 | 3/2007 | Duncan et al. |
| 7,236,822 B2 | 6/2007 | Dobak, III |
| 7,242,985 B1 | 7/2007 | Fridman et al. |
| 7,263,400 B2 | 8/2007 | Helfinstine et al. |
| 7,289,852 B2 | 10/2007 | Helfinstine et al. |
| 7,483,748 B2 | 1/2009 | Torgerson et al. |
| 7,493,159 B2 | 2/2009 | Hrdlicka et al. |
| 7,526,338 B1 | 4/2009 | Gill et al. |
| 7,551,964 B2 | 6/2009 | Dobak, III |
| 7,647,111 B2 | 1/2010 | Ries et al. |
| 7,680,540 B2 | 3/2010 | Jensen et al. |
| 7,702,385 B2 | 4/2010 | Moffitt et al. |
| 7,715,912 B2 | 5/2010 | Rezai |
| 7,805,197 B2 | 9/2010 | Bradley |
| 7,813,809 B2 | 10/2010 | Strother et al. |
| 7,937,158 B2 | 5/2011 | Erickson et al. |
| 8,024,035 B2 | 9/2011 | Dobak, III |
| 8,190,259 B1 | 5/2012 | Smith et al. |
| 8,260,424 B2 | 9/2012 | Moffitt et al. |
| 8,495,640 B2 | 7/2013 | Krauss |
| 8,509,906 B2 | 8/2013 | Walker et al. |
| 8,571,677 B2 | 10/2013 | Torgerson et al. |
| 2003/0125773 A1 | 7/2003 | Havel et al. |
| 2003/0171685 A1 | 9/2003 | Lesser et al. |
| 2003/0204221 A1 | 10/2003 | Rodriguez et al. |
| 2003/0204224 A1 | 10/2003 | Torgerson et al. |
| 2003/0204225 A1 | 10/2003 | Heathershaw et al. |
| 2004/0098067 A1 | 5/2004 | Ohta et al. |
| 2005/0010625 A1 | 1/2005 | Andrews |
| 2005/0027325 A1 | 2/2005 | Lahti et al. |
| 2005/0179458 A1 | 8/2005 | Chen et al. |
| 2006/0259098 A1 | 11/2006 | Erickson |
| 2007/0078498 A1 | 4/2007 | Rezai et al. |
| 2007/0200576 A1 | 8/2007 | Laurent et al. |
| 2007/0213783 A1 | 9/2007 | Pless |
| 2008/0177351 A1 | 7/2008 | Fang et al. |
| 2009/0024189 A1* | 1/2009 | Lee ................ A61N 1/36017 607/66 |
| 2009/0149917 A1 | 6/2009 | Whitehurst et al. |
| 2009/0256583 A1 | 10/2009 | Chen et al. |
| 2009/0265153 A1 | 10/2009 | Mazeau et al. |
| 2009/0326624 A1 | 12/2009 | Melse et al. |
| 2010/0016850 A1 | 1/2010 | Edoute et al. |
| 2010/0063555 A1 | 3/2010 | Janzig et al. |
| 2010/0274318 A1 | 10/2010 | Walker et al. |
| 2011/0029040 A1 | 2/2011 | Walker et al. |
| 2011/0077717 A1 | 3/2011 | Poletto |
| 2011/0160810 A1 | 6/2011 | Griffith |
| 2011/0184496 A1 | 7/2011 | Kallmyer |
| 2011/0208265 A1 | 8/2011 | Erickson et al. |
| 2011/0270363 A1 | 11/2011 | Schramm et al. |
| 2012/0071951 A1 | 3/2012 | Swanson |
| 2012/0197330 A1 | 8/2012 | Crutchfield et al. |
| 2012/0245664 A1 | 9/2012 | Smith et al. |
| 2012/0265272 A1 | 10/2012 | Judkins |
| 2013/0096641 A1 | 4/2013 | Strother et al. |
| 2013/0197615 A1 | 8/2013 | Rundle et al. |

FOREIGN PATENT DOCUMENTS

| | | |
|---|---|---|
| TW | 426868 | 3/2001 |
| WO | WO 03090849 | 11/2003 |

OTHER PUBLICATIONS

European Application No. 12163517.1, Extended European Search Report dated Aug. 8, 2012, 8 pgs.

Gwilliam, James Christian, et al., "A Charge-Balanced Pulse Generator for Nerve Stimulation Applications", Journal of Neuroscience methods, vol. 168, , pp. 146-150, (2008).

Kataoka, Kenichi, et al., "Contact Properties of Ni Micro-Springs for MEMS Probe Card", IEEE, pp. 231-235 (2004).

Sit, Ji-Jon, et al., "A Low-Power Blocking capacitor-Free Charge-Balanced Electrode-Stimulator Chip with Less Than 6 Na Dc Error for 1-ma Fill-Scale Stimulation", pp. 172-183 (2007).

Hottowy, Pawel, et al., "An Integrated Multichannel Waveform Generator for Large-Scale Spatio-Temporal Stimulation of Neural Tissue" Analog Integrated Circuits and Signal Processing, vol. 55, pp. 239-248 (2008).

European Search Report, European Extended Search Report, Application No. 12163520.5 dated Jul. 4, 2012, 7 pages.

European Search Report; European Extended Search Report, Application No. 12163512.2, dated Jul. 27, 2012, 9 pages.

European Search Report; European Extended Search Report, Application No. 15170882.3 dated Sep. 4, 2015, 8 pages.

* cited by examiner

ARBITRARY WAVEFORM GENERATOR AND NEURAL STIMULATION APPLICATION WITH SCALABLE WAVEFORM FEATURE AND CHARGE BALANCING

CROSS-REFERENCES TO RELATED APPLICATIONS

This application is a divisional application of U.S. patent application Ser. No. 13/828,102, filed on Mar. 14, 2013, which is a continuation-in-part of U.S. patent application Ser. No. 13/081,896 filed on Apr. 7, 2011, now issued as U.S. Pat. No. 8,996,115, and also a continuation-in-part of U.S. patent application Ser. No. 13/081,936 filed on Apr. 7, 2011, now issued as U.S. Pat. No. 8,874,219, as well as a continuation-in-part of U.S. patent application Ser. No. 13/082,097 filed on Apr. 7, 2011, now issued as U.S. Pat. No. 8,996,117, the contents of each of which are herein incorporated herein by reference in their respective entireties.

FIELD OF THE INVENTION

This application relates generally to a device for generating waveforms, and more specifically, this application relates to an implantable medical device for generating waveforms for spinal cord stimulation. This application also related generally to a method for charge balancing, and more specifically, this application relates to an implantable medical device for active charge balancing arbitrary waveforms for spinal cord stimulation.

BACKGROUND OF THE INVENTION

Programmable pulse generating systems are used to treat chronic pain by providing electrical stimulation pulses from an electrode array placed in or near a patient's spine. Such Spinal Cord Stimulation (SCS) is useful for reducing pain in certain populations of patients. SCS systems typically include one or more electrodes connected to an External Pulse Generator (EPG) or an Implanted Pulse Generator (IPG) via lead wires. In the case of an EPG, the lead wires must be connected to the EPG via an exit from the body. The pulse generator, whether implanted or external, generates electrical pulses that are typically delivered to the dorsal column fibers within the spinal cord through the electrodes which are implanted along or near the epidural space of the spinal cord. In a typical situation, the attached lead wires exit the spinal cord and are tunneled within the torso of the patient to a sub-cutaneous pocket where the IPG is implanted, or the wires exit the patient for connection to the EPG.

Neural stimulators for SCS to date have been limited to waveform shapes dictated by their circuitry. Most emit relatively simple rectangular or trapezoidal stimulation phases with exponential, clamped-exponential, or rectangular charge recovery phases. Similar waveform limitations typically exist for stimulators used in other medical applications such as cardiac implants, cochlear implants, etc. Nevertheless, it is desirable that other waveform shapes be available, as such shapes may be useful in controlling which nerve fibers respond to a stimulation pulse. By selecting particular fibers for response, the therapeutic benefit of neural stimulation can be increased and side-effects decreased. Additionally, other waveform shapes may achieve effective stimulation results while requiring less energy than traditional waveforms, thereby extending the battery life of the stimulator.

Currently, the principal way to select a stimulation waveform was to design a stimulator that emitted that waveform as its only form, or as one of a handful of parameter-driven options. For example, a stimulator may be provided that adjusts the charge recovery phase to either an exponential or a rectangular shape based on the pulse rate selected by the user. The stimulation phase is typically provided with only a fixed rectangular shape. In contrast, it would be useful to allow the use of an arbitrary waveform shape for the either the stimulation phase, charge recovery phase, or both, rather than being limited to a simple waveform shape designed into the circuitry.

Desired is a capability of producing complex waveform shapes, whether or not they are inherently piecewise-linear, in particular with an ability to adjust amplitudes and pulsewidths simply and efficiently, such as, for example, by providing an ability to rescale portions of a waveform in time, thus adjusting pulsewidths on the fly without having to re-compute the waveform samples.

An additional problem with existing neural stimulators is that they include DC blocking capacitors to balance charges and prevent the flow of direct current to the body tissue. Balancing such charges and blocking dc current flow is considered desirable for safety reasons. Desired is an approach that removes or reduces the need for such blocking capacitors by inherently balancing the stimulation waveform charges and preventing the flow of direct current.

SUMMARY OF THE INVENTION

Disclosed herein is a device/system capable of producing complex waveform shapes, whether or not they are inherently piecewise-linear. It is also capable of adjusting amplitudes and pulsewidths simply and efficiently.

Also disclosed is a device/system that completely or partially removes the need for blocking capacitors by inherently balancing the stimulation waveform current and preventing the flow of direct current, such as by providing a charge balancing phase that has a charge that is equivalent but inverse to that delivered during the stimulation phase.

Further disclosed herein is a device/system that can rescale portions of a waveform in time, thus adjusting pulsewidths, directly without having to recompute the waveform samples. Such a device/system can also generate the waveform, for example by using data from one or more small template waveshapes stored in a small memory, permitting it to use much less memory for complex waveforms.

Provided are a plurality of embodiments the invention, including, but not limited to, a method for providing a therapy to a patient, the method comprising the steps of:
  storing a plurality of discrete samples of a waveform in a memory;
  defining a step size;
  retrieving a series of the plurality of the samples from the memory, based on the step size;
  reconstructing at least a part of the waveform using the retrieved series of samples; and
  providing a stimulation pulse with at least a substantial portion in a shape resembling the reconstructed waveform for stimulating a stimulation region of the patient.

Also provided is a method for balancing charges provided by a medical device for providing a therapy to a patient, the method comprising the steps of:

providing a first portion of a stimulation waveform for stimulating a stimulation region of a patient, the first portion of the stimulation waveform inducing an electrical charge at the stimulation region of the patient; and providing a second portion of a stimulation waveform for stimulating the stimulation region of the patient after providing the first portion of the stimulation waveform for substantially canceling the electrical charge at the stimulation region of the patient, wherein the second portion of the stimulation waveform is primarily comprised of a portion having a shape other than a square wave and other than a decaying exponential.

Further provided is a method for providing a therapy to a patient, the method comprising the steps of:

providing a waveform generating circuit for generating a waveform of a desired shape having an amplitude and a duration;

defining a scaling factor;

using the scaling factor for scaling the waveform generated by the waveform generating circuit, such that both the amplitude and the duration of the waveform is adjusted using the scaling factor; and providing a stimulation pulse including at least a substantial portion that is based on the scaled waveform having shape resembling the desired shape of the waveform for stimulating a stimulation region of the patient.

Also provided is a method for balancing charges provided by a medical device for providing a therapy to a patient, the method comprising the steps of:

providing a first portion of a stimulation waveform for stimulating a stimulation region of a patient, the first portion of the stimulation waveform inducing a first electrical charge at the stimulation region of the patient;

providing a second portion of the stimulation waveform determined based on the first portion of the stimulation waveform for stimulating the stimulation region of the patient after providing the first portion of the stimulation waveform, the second portion of the stimulation waveform having a shape other than a square wave or a decaying exponential and substantially canceling the first electrical charge at the stimulation region of the patient; and providing a passive recovery phase after providing the second portion of the stimulation waveform for removing any residual charge at the stimulation region of the patient.

Still further provided is a method for balancing charges provided by an implantable medical device for providing a therapy to a patient at a stimulation region near the spine of a patient, the method comprising the steps of:

providing an electrode near the stimulation region;

providing an implanted waveform generating device connected to the electrode;

the waveform generating device generating a first portion of a stimulation waveform for stimulating the stimulation region using the electrode, the first portion of the stimulation waveform inducing a first electrical charge at the stimulation region; and the waveform generating device generating a second portion of the stimulation waveform based on the first portion of the stimulation waveform for stimulating the stimulation region using the electrode after providing the first portion of the stimulation waveform, with the second portion of the stimulation waveform substantially canceling the first charge at the stimulation region of the patient, wherein the second portion of the stimulation waveform includes a substantial portion having a shape other than a square wave and other than a decaying exponential.

Also provided is a method for balancing charges provided by an implantable medical device for providing stimulation to a patient at a stimulation region of the patient, the method comprising the steps of:

providing an electrode near the stimulation region;

providing a waveform generating circuit connected to the electrode;

the waveform generating circuit generating a first portion of a stimulation waveform by converting digital data into an analog signal for stimulating the stimulation region using the electrode, the first portion of the stimulation waveform inducing a first electrical charge at the stimulation region;

the waveform generating circuit generating a second portion of the stimulation waveform by converting digital data based on the first portion of the stimulation waveform into an analog signal for stimulating the stimulation region using the electrode after providing the first portion of the stimulation waveform, the second portion of the stimulation waveform including a substantial portion having a shape other than a square wave and other than a decaying exponential with the second portion of the stimulation waveform substantially canceling the first electrical charge at the stimulation region of the patient, wherein no substantial residual induced electrical charge remains in the stimulation region subsequent to the second portion of the stimulation waveform.

Also provided is medical waveform generator, comprising: a waveform generator adapted for generating an output waveform comprised of any of a plurality of differently shaped waveforms; a time scaling circuit configured for time scaling the generator output waveform; a current divider configured for scaling the amplitude of the time scaled generator output waveform for outputting an amplitude scaled output waveform; and an amplifier configured for amplifying the amplitude scaled output waveform for outputting a stimulation waveform.

In addition is provided medical waveform generator comprising: a plurality of electrode outputs; a waveform generator configured for generating an output waveform comprised of any of a plurality of differently shaped waveforms; a time scaling circuit configured for inputting a signal into the waveform generator for time scaling the generator output waveform; a current divider configured for scaling the amplitude of the generator output; a plurality of amplifiers, each one of the amplifiers being configured for amplifying an output of the current divider for outputting a stimulation waveform corresponding to a different one of the electrode outputs; and a controller configured for controlling the waveform generator, the time scaling circuit, the current divider, and the amplifiers for generating the stimulation waveform having the desired shape(s), amplitude, and time scale.

Also provided is a medical waveform generator comprising: a waveform generator configured for generating an output waveform comprised of any of a plurality of differently shaped waveforms, the waveform generator including: at least one square wave generator configured for generating one or more of the differently shaped waveforms shaped as square waves, and a plurality of memories, each one of the memories storing a waveform template for generating a different one of the differently shaped waveforms not shaped as square waves; and an amplitude scaling circuit configured for scaling the amplitude of the generator output waveform for outputting a stimulation waveform.

Further provided is a device for stimulating a stimulation region of a patient comprising: a waveform generation circuit for providing a stimulation waveform by converting digital data into an analog signal for providing to the stimulation region of the patient; and a control device for controlling the waveform generation circuit.

The above control device can be adapted for directing the waveform generation circuit for generating a charge canceling waveform for providing to the stimulation region of the patient subsequent to providing a stimulation waveform to the stimulation region, such that the charge canceling waveform is derived based on the shape of the stimulation waveform.

In addition is provided a device for stimulating a stimulation region within a patient comprising: an electrode adapted to be provided near the stimulation region; a waveform generation device adapted to be implanted in the patient, the waveform generation device including: a waveform generation circuit connected to the electrode for providing a stimulation waveform to the electrode by converting digital data into an analog signal, and a control device for controlling the waveform generation circuit.

The above control device can be adapted for directing the waveform generation circuit for generating a charge canceling waveform by converting digital data into an analog signal for providing to the stimulation region within the patient subsequent to providing the stimulation waveform, such that the charge canceling waveform substantially cancels an electrical charge induced to the stimulation region by the stimulation waveform.

The above control device can also adapted for accepting control inputs for providing a second stimulation waveform having a different shape than the first stimulation waveform, with the control device being further adapted for providing a second charge canceling waveform specifically based upon the second stimulation waveform for canceling the charge provided to the stimulation region by the second stimulation waveform.

Still further provided is a system for stimulating a stimulation region of a patient utilizing the above devices and/or methods. Such a system can also be provided to include one or more of an electrode adapted to be provided near the stimulation region; a waveform generation device such as one of the above disclosed devices or such as a device for performing one or more of the above methods; an external device for wirelessly connecting to the control device for controlling an operation of the waveform generation device; and/or an external power source for connecting inductively to the energy storage device for recharging the energy storage device when the energy storage device is in a vicinity of the external power source.

Also provided are additional embodiments of the invention, some, but not all of which, are described hereinbelow in more detail.

BRIEF DESCRIPTION OF THE DRAWINGS

The features and advantages of the examples of the present invention described herein will become apparent to those skilled in the art to which the present invention relates upon reading the following description, with reference to the accompanying drawings, in which.

DETAILED DESCRIPTION OF THE EXAMPLE EMBODIMENTS

Disclosed is a device, or system of devices cooperating with each other, for providing a flexible and highly adaptable stimulation waveform, such as might be used for medical purposes such as spinal stimulation (such as for pain reduction, for example). This system includes a neurostimulation pulse generator that uses digital waveform synthesis techniques to generate stimulation pulses with programmable waveshapes.

Figure 1:
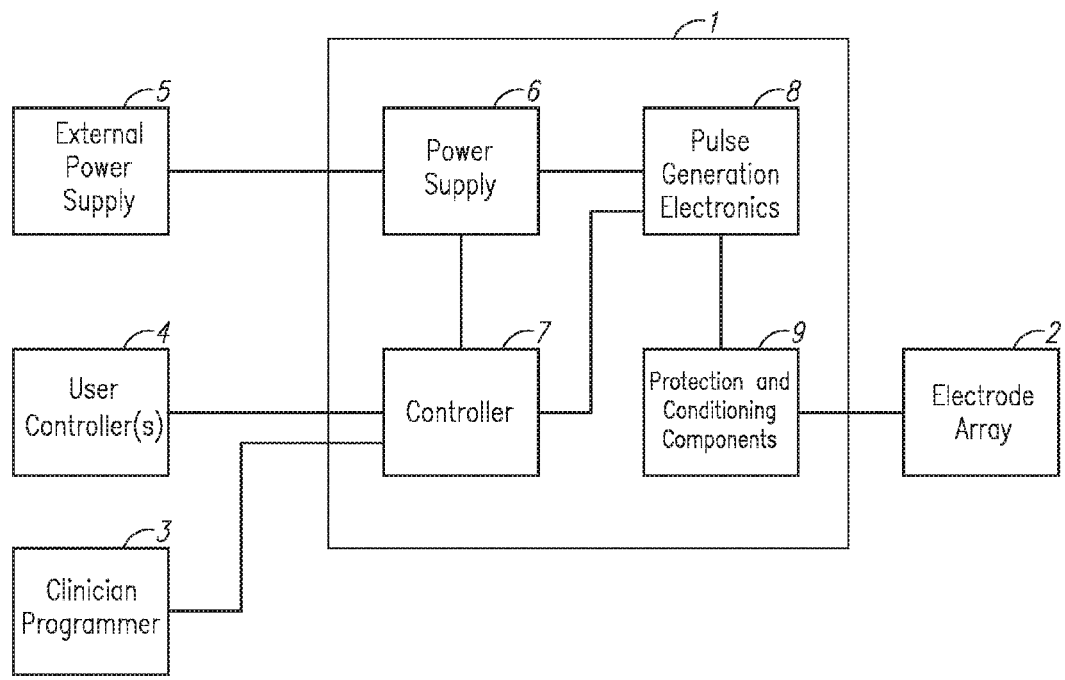
FIG. 1 is a block diagram showing a high-level structure of an example embodiment.

FIG. 1 is a generic diagram of an example stimulation system. Such a system includes a Pulse Generator (PG) component 1, a set of two or more electrodes (which may include the PG's enclosure) 2, external programming and user controlling devices 3, 4, and a connection to an external power supply 5. The Pulse Generator 1 is typically generally comprised of an internal power supply 6, a controller 7. Pulse Generator electronics 8, and a protection circuit 9.

Figure 2:
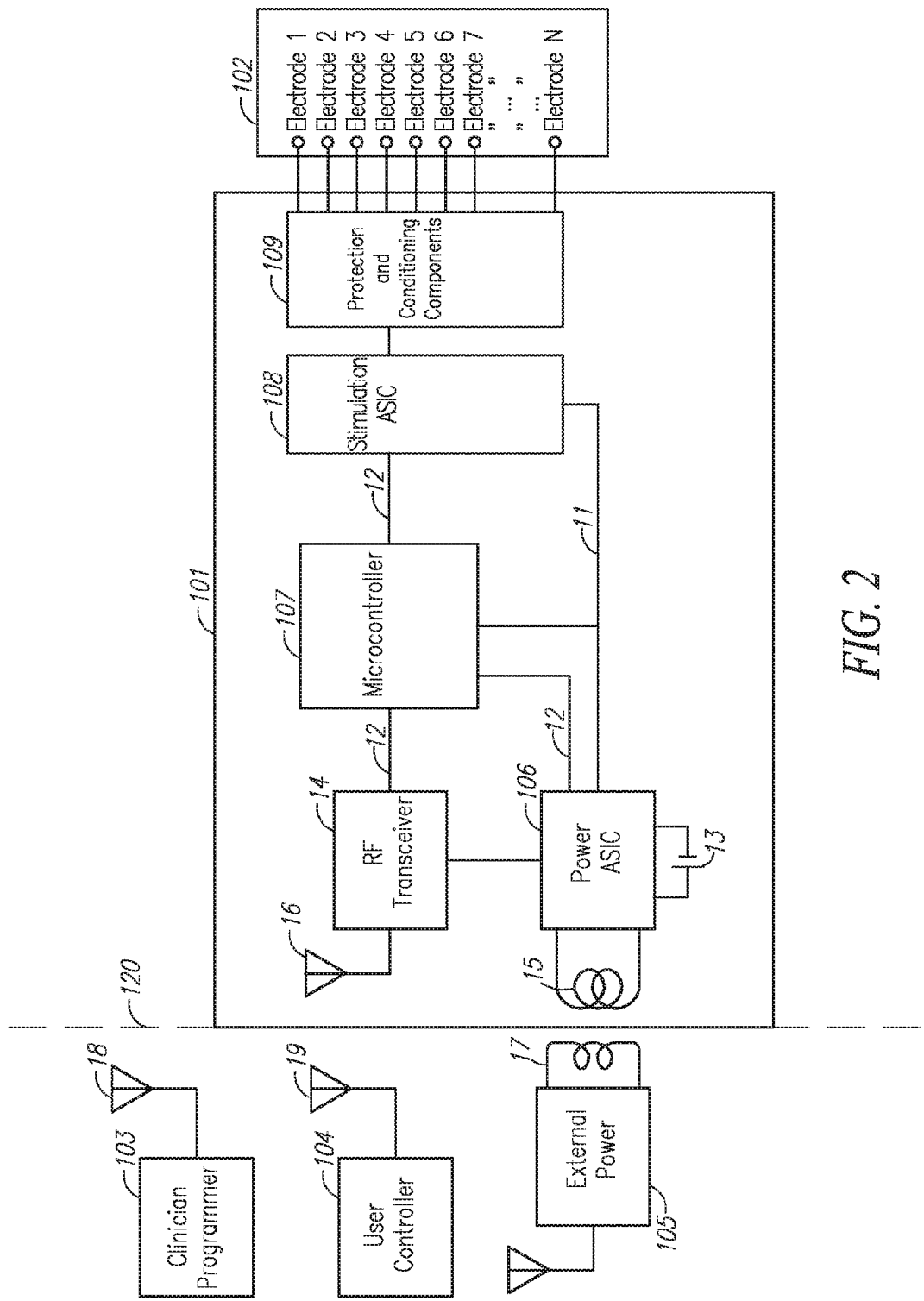
FIG. 2 is a block diagram showing a more detailed structure of a possible construction of the example embodiment used as an implantable pulse generator.

FIG. 2 shows a more specific example system where most of the components for generating the stimulation waveform are implanted in a patient for providing medical therapy by utilizing an implantable PG (IPG) 101 that could utilize the disclosed features. This system is comprised of the IPG 101 that includes a stimulation ASIC 108 and protection components 109. The IPG 101 is further comprised of a microcontroller 107 for controlling the functions of the IPG via the control bus 12, and a power ASIC 106 for powering the components via a power bus 11. Because this implantable system avoids the need for any components or wires that exit the body of the patient 120, the IPG 101 includes an RF transceiver (transmitter/receiver) 14 with an antenna 16 for allowing the IPG to communicate with devices external to the patient's body, such as a clinician programmer 103 and user controller(s) 104, which also have antennas 18 and 19, respectively, to communicate with the transceiver 14 via a wireless protocol. Furthermore, the IPG also includes an embedded power supply including a power ASIC 106 for conditioning the device power, a (long life) rechargeable battery 13, and a secondary inductive coil 15 (or some other means) for receiving power from an external source outside the body of the patient 120. A corresponding external power supply 105 would typically require a corresponding primary charging coil 17 to complete the power connection to the embedded power supply to charge the battery 13. The IPG 101 is connected to one or more electrode arrays 102 including a plurality of electrodes via a header (not shown) connected via feedthroughs (not shown) to the protection components 109. The IPG 101 is provided in a hermetically sealed case made of, or coated by, human implantable compatible materials, and requiring only that the contacts attached to the lead body of the electrode array(s) be electrically connectable to the IPG through the header. The electrode leads and electrodes themselves, along with portions of the header that are exposed to the patient, must all be made of, or coated by, materials that are compatible with implantation in the human body.

Figure 3:
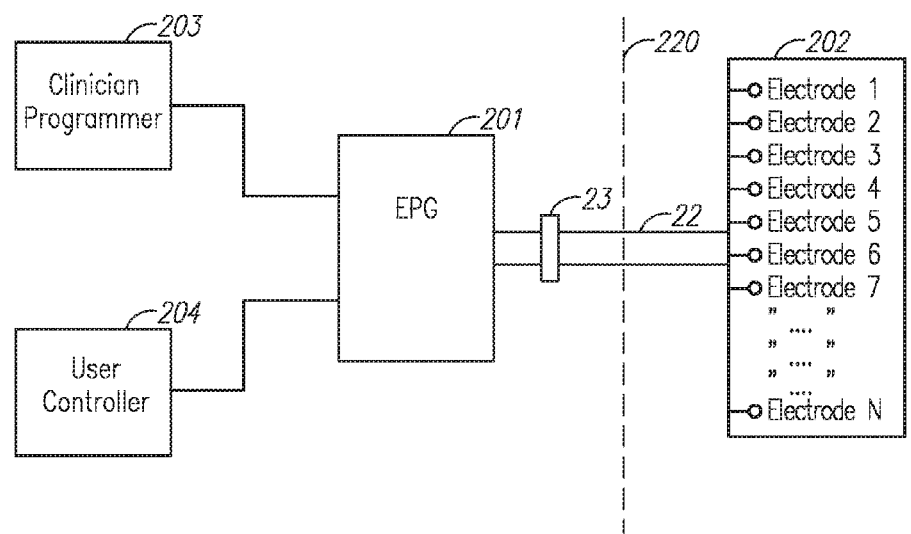
FIG. 3 is a block diagram showing an example system used as an external pulse generator.

FIG. 3 shows an example system that can be provided with similar capabilities, but without requiring an implantable PG. Instead, the system of FIG. 3 uses an external PG (EPG) 201 that is provided outside of the body of the patient 220. The EPG 201 can be comprised of similar components as that of the IPG 101, except that it need not be made of implantable materials. Instead, the EPG 201 is connected to the electrode array 202 via a percutaneous lead 22 that must exit the body. The lead 22 is then connected to the EPG 201 via a connector 23. The EPG 201 can be directly connected to the corresponding clinician programmer 203 and user controller 204, or a wireless connection similar to that of the IPG 101 could also be used. The EPG can be powered via an internal battery or connected to an external power source, as desired.

One end of the percutaneous lead 22 is typically surgically implanted in or near the tissue to be stimulated. The other end is brought through a wound in the skin, and can be connected to the EPG when electrical stimulation is needed. The implanted end of the Percutaneous Lead typically includes electrode surfaces similar to those on the implanted lead(s). The EPG may be designed to be mobile, such that it can be carried by the patient, such as by mounting on a belt. In such a case, a battery would prove useful to increase mobility.

An Implantable Pulse Generator is surgically placed inside the body along with one or more implanted leads (as shown by example in FIG. 2 and discussed above). One end of each implanted lead (often called the "proximal" end) is electrically and physically connected to the IPG via the header, while the other end (often called the "distal" end) is placed in or near the tissue to be electrically stimulated. The distal end includes one or more exposed electrode surfaces, electrically connected to the IPG, that transfer the electrical stimulation pulses to the tissue.

Outside the body, the external power supply is used to transfer power to the IPG, either for charging a battery or capacitor inside the IPG or providing direct power for the IPG's electronics. This is done via the charging coil, which is placed over or near the area where the IPG is implanted, and forms the primary coil of a transformer with the secondary coil inside the IPG, although a separate coil electrically connected to the IPG but somewhat remote from the IPG could be used. The two coils, coupled inductively, provide power transfer through the skin. The external power supply itself can be powered by a battery to allow for patient mobility, or it may also draw power from a mains power source.

Also outside the body, the clinician programmer is used to program the IPG, configuring it for the particular patient and defining the electrical stimulation therapy to be delivered to the target tissue. The clinician programmer is typically highly functional, allowing IPG programs to be substantially modified by updating programs and/or data stored in memory in the IPG, to allow great flexibility in programming the IPG.

The user controller is used to control the operation of the IPG in a manner limited by its programming. Thus, the user controller is typically less functional than the clinician programmer. The user controller can alter one or more parameters of the electrical stimulation therapy to adjust the therapy to the liking of the patient, depending on the IPG's program and configuration as set with the clinician programmer.

The operation of an EPG (as shown by example in FIG. 3 and discussed above) is similar, with the exception that there is typically no need for inductive transfer of power as direct cable connections can be used to recharge any battery, for example, and the electrode leads must pass through the body to connect to the EPG.

Pulse generators (PGs), whether implanted pulse generators (IPGs) or external pulse generators (EPGs), have, to date, used waveforms that are generally rectangular for the stimulation phase of the waveform and either rectangular or exponential for the charge recovery phase. However, waveform shapes other than these basic choices may be effective in selecting which nerve fibers are activated by an EPG or IPG. For example, one waveform shape may be preferable for selecting large-diameter fibers, while another shape may be preferable for small-diameter fibers. Because the fiber diameter in a given nerve is related to the function of that fiber, improved selectivity of one nerve fiber over another can improve the likelihood of achieving the desired results of neural stimulation, such as pain relief, with less occurrence of undesirable side-effects such as pain or muscle spasms.

For safety reasons, most PGs use charge-balanced waveforms. A charge-balanced waveform is one in which the effective DC current is zero or nearly zero. For example, various national and international standards limit the net DC current to 10 µA (AAMI/ANSI NS-14, incorporated by reference), or 0.1 µA (ISO 45502-2-1, incorporated by reference), depending on the intended use of the PG. A charge-balanced pulse is made up of at least two phases of stimulation current, each phase having a single polarity, such that the integral of the current over time of all the phases, representing accumulated electrical charge, equals zero. Typically, there are two phases, the first phase being intended to create the desired effect in the tissue, and the second phase, of opposite polarity, used to bring the waveform into charge balance.

To prevent tissue damage and/or electrode corrosion, charge delivered on one electrode is usually recovered on the same electrode, because any residual charge can change the chemical composition of the tissue near the electrode. It does not take much imbalance to get significant electrode corrosion, which is particularly problematic in implanted devices.

Typically, charge-balancing is done with the aid of DC blocking capacitors that are provided in the conditioning/protection circuit, which serve the function of integrating the charge transferred in the stimulation phases up to a given time. By bringing the voltage on the capacitor to its original value during the charge recovery phase of the pulse, the integral of the current is brought to zero, assuring charge balance. These DC blocking capacitors are bulky, which runs counter to the goal of making a PG as small as possible (in particular, for an IPG). DC blocking capacitors have other drawbacks as well, as in some designs, the DC leakage through the capacitor dielectric and/or insulation results in a DC current through the tissue, the opposite of the intended reason for including the capacitors.

Thus, provisions for charge balancing without requiring DC blocking capacitors is discussed herein as well. This feature permits the construction of smaller PGs and eliminates the risk of DC leakage through the capacitors.

The waveform generation core is the primary component that is modified by this disclosure, and can be comprised of waveform generation circuitry including any or all of the following components: one or more memories to store waveshape templates, a phase accumulator, a step-size register, one or more waveshape calculation logic circuits, and a clock source. Which of these devices are utilized depends on the desired implementation, any of which may be omitted where not needed, and any of which can be replicated as desired. Conditioning/protection components may also be used, although at least some embodiments seek to avoid such components through an active protection and charge dissipation methodology. These components are described in more detail, below. An example operation of a device comprising at least one of all of these components can be generally described, along with at least one medical application.

Provided is the utilization of a waveform shape stored in memory and used as a template for generating shaped stimulation pulses. These templates can be programmed via the clinician programmer, which may have a selection of available shape templates for the clinician to choose from, or the templates may be programmed into the device during manufacture. The memory is structured such that each memory location represents a time step, and the value stored in each memory location represents the amplitude at that time step. Basically, the waveform is generated by addressing a memory to retrieve some number of waveform samples stored in a memory for any of the desired waveform shapes, in the following manner: A waveform is to be constructed using one or more phases for creating portions of the stimulation pulse waveform, including both the stimulation phase and the charge recovery phase. At the start of each phase of the stimulation pulse, a phase accumulator is set to a programmed offset value as a start address used to retrieve a waveform sample value from memory. This offset value sets the sample, from the waveshape template stored in memory, that will start the pulse.

As the phase continues, at each sample time the phase accumulator is incremented by a step size stored in a step-size register to calculate the next address value. This next address value is used to select an additional sample from the stored waveshape template, and the process is iterated again to retrieve additional amplitude samples from the waveshape template that make up the current phase of the pulse. The step size in the example is a fixed-point number that can have both integer and fractional components, if desired. By permitting fractional increments in the step size, it is possible to generate waveshape durations of any integer length, not just those that divide evenly into the number of samples in the waveshape template. Also, if the fixed-point step size is less than one, the pulse width will be made longer than the number of samples in the template; samples can then be automatically be duplicated, as necessary, to extend the pulse. This allows the memory size required for reasonable fidelity to be optimized for the typical pulse width used by the therapy, while still allowing very short or very long pulse widths to be possible.

The output from the phase accumulator is used as an index into a programmably selected waveform memory as described above, or it can be used to index a shape-generating logic circuit, depending on the current implementation and/or desired output waveform. A waveform memory would be used to look up a waveform sample that was stored in advance at the indexed location of the memory and output the desired waveform shape, which allows a great flexibility in the shapes of waveforms. A single register, in contrast, which outputs the same (constant) programmed value regardless of the index could be used to generate rectangular waveforms. A shape logic circuit, in contrast, computes a fixed mathematical function based on the input index (or based some other input or internal function) and outputs the result as a waveform shape, which may be particularly useful for situations where waveforms that are provided by simple mathematical equations are desired (such as exponentials, ramps, sine waves, etc.).

The output from the waveform memory or waveform calculation logic (whichever was chosen) then drives a digital-to-analog converter (DAC), called a "waveform DAC", which creates a reference current (or voltage). This reference current (or voltage) is in turn used as the input of several multiplying digital-to-analog converters, called "amplitude multipliers". The data input of the converters comes from programmable amplitude registers for that phase of the stimulation waveform. The result of the multiplication is a current (though a voltage could also be generated), positive or negative (or equivalently, sink or source), which is output to the electrodes in contact with body tissue. By adjusting the values in the amplitude registers, the amount and polarity of current (or voltage) output to each electrode can be adjusted, thus shaping the electric field generated by the phase. Although the examples provided herein focus on the use of a single waveform generation circuit that can drive a plurality of electrodes by driving the output into a number of amplitude-multiplying DACs, replication of the waveform generation circuit can be used to provide additional flexibility to the output, if desired, such that any given waveform generation circuit may independently drive a subset of one or more electrodes. In such a situation, the circuits could be modified to share memories of waveform shape templates to reduce unnecessary replication.

The stimulation waveform is divided into a series of pulses, each of which is divided into a series of unipolar phases. Each phase has a programmable repetition count (to repeat the phase a number of times, if desired) and a programmable delay before the next phase. Circuitry in the stimulator automatically sequences the phases and their repetitions, and hence, the pulses that are made up from the phases. This allows a single stimulation pulse to have more than two phases defined for it. This structure allows for "n-lets", or pulses that have repeated stimulation phases, as well as one or more "pre-pulses", where one or more additional phases are added prior to the stimulation phase to provide pre-polarization.

Programmable dividers for amplitude (each called a "current divider") and time (each called a "clock divider") can be used to scale a waveform simultaneously in time and amplitude in such a way that permits charge balancing in cases where the same shape is used for both the stimulus and charge recovery phases. The current and clock dividers can be omitted or can be included but unused, if desired. In such a case, the current divider and clock divider registers could be programmed appropriately to provide charge balancing.

The pulse generator typically includes amplitude multipliers for every channel on the device.

Pulse Generator Architecture

The improvements discussed herein can be used with an Implantable Pulse Generator (IPG) as shown in FIG. 2 (discussed above) or an External Pulse Generator (EPG) as shown in FIG. 3 (also discussed above). The description below will focus on example implementations using the IPG based system, but an EPG system could be easily adapted in a similar manner.

As described above, a block diagram of the internal functions of an example IPG system is shown in FIG. 2.

The microcontroller 107, which is implemented using a programmable controller as is known in the art, controls at least the embedded components of the system, stores stimulation program information, and performs other control and management functions, some of which are disclosed herein. The RF Transceiver 14 implements bidirectional digital communications at radio frequencies in the IPG with external devices as desired. The attached antenna 16 is used to transmit and receive these radio signals, by which the IPG communicates with such components as the User Controller 104, Clinician Programmer 103, and/or External Power source 105, among other possible devices.

The Power ASIC 106 is connected to the Battery 13, which provides electrical power to the powered internal components. The Power ASIC 106 is also connected to the secondary coil 15, by which it receives electrical energy inductively coupled through the patient's body from the primary charging coil 17. The Battery 13 may be either primary or rechargeable, or may be omitted in lieu of some other power source. If the battery 13 is a primary battery, the external power unit 105, the charging coil 17 and secondary coil 15 may be omitted. Typically, a secondary battery that is rechargeable is desirable to lengthen the useful life of the battery and avoid additional surgeries to replace the pulse generator or its components. Other power supplies in the future may prove useful to replace the battery implementation.

The Stimulation ASIC 108 includes the stimulation pulse waveform generation circuitry. This ASIC 108 is controlled by the microcontroller 107 and has power supplied by the Battery and/or Secondary Coil via the Power ASIC.

The Protection Components 109, if used, may include DC blocking capacitors and electrical transient suppression components, among other components. Together, these components protect the tissue from unwanted electrical signals and DC currents, and protect the PG from external electrical events such as electrostatic discharge, defibrillation, or electrocautery. In some embodiments, particularly those discussed in a related application, some of these components might be reduced (in size and/or quantity) or eliminated through the use of active charge balancing techniques. Thus, for at least some embodiments (in particular embodiments exclusively using active charge balancing), the waveform generation core may consist of only the stimulation ASIC, along with any supporting components, if necessary.

Waveform Generation Core

Figure 4:
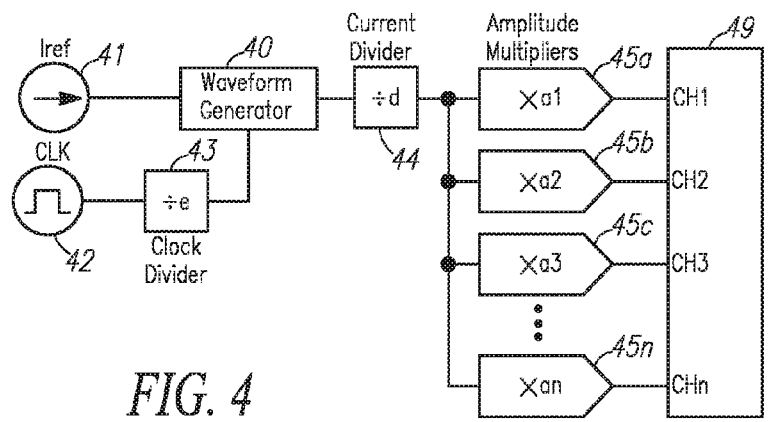
FIG. 4 is a schematic of one example implementation of part of a pulse generator circuit and supporting components in an example system.
Figure 5:
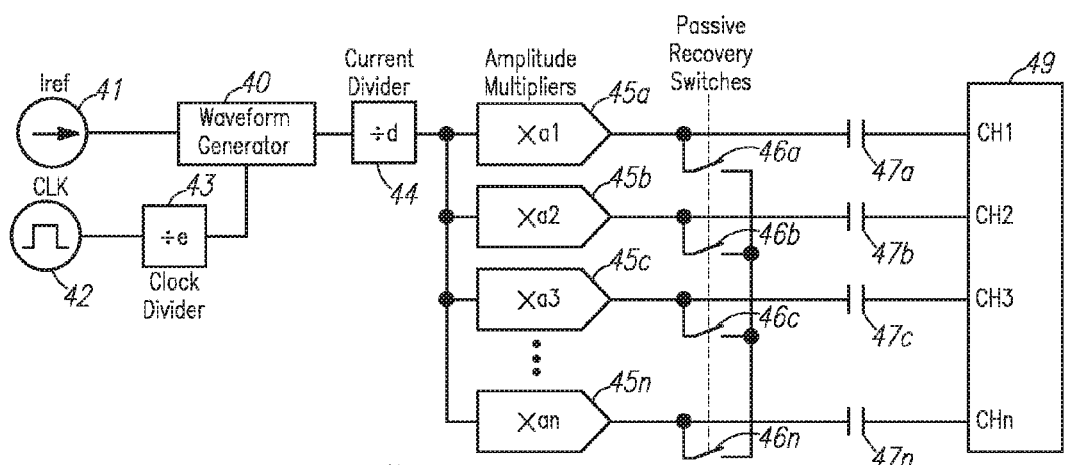
FIG. 5 is a schematic of another example implementation of part of a pulse generator circuit and supporting components in another example system.

FIGS. 4 and 5 show generalized embodiments of potential waveform generation core designs for use in providing the improved waveform generation capabilities. In general, power and control connections are not shown in these figures, as their use is within the skill of the art based on this discussion.

FIG. 4 shows a simplified block diagram of a generic waveform generation core of a stimulator system incorporating the waveform generation improvements. A reference generator "Iref" 41 that is a reference current source sets the over-all amplitude scaling of the system. A clock signal CLK 42, sets the over-all time scaling of the system, and the Clock Divider 43 scales the clock by a configurable division factor. The Waveform Generator 40, representing the core of the waveform generation function, outputs the shape of each phase of the pulse, creating the "normalized waveform" that basically forms the stimulation waveform into its desired shape. The Current Divider 44 scales the output of the Waveform Generator 40 by performing a division operation, creating the "scaled waveform". Finally, the Amplitude Multipliers 45a~45n (typically one per channel) multiply the scaled waveform by a configurable amplitude and polarity for each individual channel CH1~CHn in the electrode array 49. The peak amplitude and polarity for each channel do not vary during a given phase of a pulse, but do change from one phase to the next. Each Amplitude Multiplier 45 has an independent current output, each of which can be used to drive a subset of one or more of the stimulation electrodes. Furthermore, multiple current outputs can be used to drive a single electrode.

FIG. 5 shows a simplified block diagram of a stimulator similar to that of FIG. 4 with the addition of DC blocking capacitors 47a~47n and passive-recovery switches 46a~46n. The addition of the blocking capacitors and passive-recovery switches allows charge balancing to be achieved in a passive manner by selectively closing the switches and connecting the capacitors to a common node. Thus, the embodiment of FIG. 5 would be more likely utilized where an active charge balance function is either not utilized, or not sufficient to completely balance the charges produced by the device, whereas the embodiment of FIG. 4 could be utilized where an effective charge balancing procedure is used.

Although not shown, the waveform generation circuitry could be replicated and provided with a multiplexor or set of switches connected to the inputs of the amplitude-multiplying DACs in order to allow different waveforms to drive various subsets of the electrodes. However, in the example, one waveform generation circuit is provided, and deemed satisfactory for many purposes.

Waveform Generator

Figure 6:
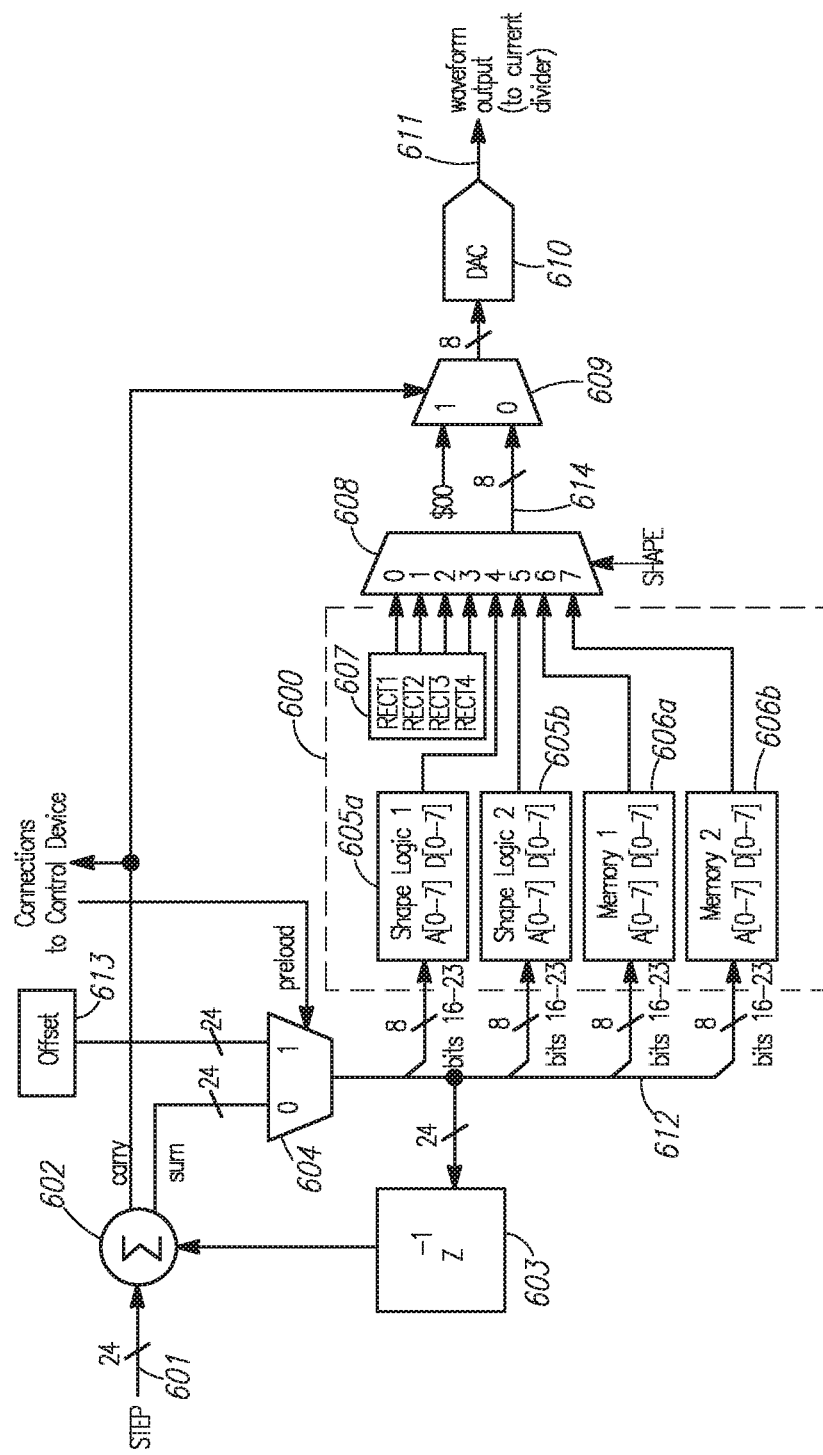
FIG. 6 is a schematic of an example implementation of a waveform generation circuit and supporting components in an example system.

The internal structure of an example embodiment of the Waveform Generator 40 is shown in FIG. 6. Again, the power connections are not shown, and only some of the control inputs most applicable to this discussion are shown in this figure.

Generally, this example waveform generator is comprised of, for example, a 24 bit input bus 601 for inputting a desired step size. A summer 602 is used to increment an address value based on the step size as the device iterates over each phase. An offset register or input 613 can be used to correct for waveform distortions that may occur for certain step sizes by being preloaded in the preload, as described below. A digital preload multiplexer 604 is used to switch between the offset at the start of the phase or the sum value to continue the phase.

The output of the preload multiplexer 604 is carried by the address bus 612 and contains the address value that is input into the delay 603 for a step delay for input into the summer 602 to increment the address by one step size. For the example embodiment, only the highest 8 bits of the address are input into the waveform generating circuit 600. Other embodiments might use the entire address, however, or may also use more or fewer bits depending on the shape fidelity required for the therapeutic application.

The waveform generating circuit 600 outputs digital values representing the desired amplitude values at each time step of the waveform, and is comprised of those shape components that will generate the desired waveform shapes. Such shape components can include one or more RECT registers 607 which generate constant values regardless of input address for generating square wave pulses. Such shape components can also include one or more shape logic circuits 605a, 605b . . . for generating waveforms based on mathematical functions, for example. Furthermore, the waveform generating circuit 600 can also be comprised of one or more memory circuits 606a, 606b . . . that contain values representing programmed shape templates of desired waveforms.

A shape multiplexor 608 is used for choosing which shape component output is desired, based on a shape control input from the microcontroller (not shown), for example. The shape multiplexor 608 output 614 is connected to a carry multiplexor 609 that is used to zero the value at the start/end of the phase (when the summer overflows, for example). A Digital to Analog converter 610 converts the 8 bit shape data value into an analog value 611 of a current or, in some embodiments, a voltage, which is then connected to dividers and/or multipliers, as desired, to scale the shape into the desired amplitude.

Example operations of the example Waveform Generator described above can now be provided. In the first cycle of waveform generation in this example, the preload input of the preload multiplexor 604 has a value of "1". This causes the initial 24-bit output on the address bus 612 to be the 24-bit value OFFSET:$00:$00. That is to say, it is a 24-bit value with an OFFSET value in the most significant eight bits, and the least significant sixteen bits all zero. In subsequent cycles the preload input to the multiplexor 604 is "0", and as a result, the 24-bit digital word "STEP" input 601 is added in the summer 602 (Σ) to the output of the unit delay 603 ($z^{-1}$) block, making a new 24-bit sum and one bit of carry. Tracing the path of the sum, one can see that it then becomes the input to the unit delay 603 ($z^{-1}$) block. Thus, with each clock cycle, the sum on the address bus 612 increases by the amount "STEP".

In the Example shown in FIG. 6, the most significant eight bits of the sum are used as the address into two memories, Memory 1 606a and Memory 2 606b, which may be any kind of digital memory such as RAM, ROM, EEPROM, Flash, or other types. The memories 606a and 606b each store a different wave shape template of a desired waveform to be generated. The address indexes the desired entry of the template for the particular clock cycle. Note that the address does not necessarily increment by one in every clock cycle. Depending on the value of STEP, it could also increment by less than one, resulting in multiple samples of a given entry in the template being used, or it could increment by more than one, resulting in only some, but not all, samples being used. Thus, an output waveform of arbitrary duration is synthesized from a wave shape template of fixed duration.

In the special case of rectangular waveforms, every element of the memory would be set to the same value. Thus, to avoid this inefficient use of memory space, the device can provide a number of rectangle registers, numbered RECT1-RECTn. In the Example of FIG. 6, four such RECT1-RECT4 registers 607 are used. Since rectangular waveforms have the same amplitude value for all addresses, it is not necessary to actually address these registers.

Similarly, it is possible to use digital logic circuits in place of a memory to generate useful waveforms. Two such logic circuits are shown in FIG. 6 as blocks Shape Logic 1 605a and Shape Logic 2 605b. For example, a rising ramp waveform may be generated by connecting the top 8 bits of the sum directly to one of the multiplexer 608 inputs (in lieu of a memory), or a falling ramp may be generated by connecting the logical inverses (using a NOT operation) of the top 8 bits to the multiplexer input. Other variations are possible, such as providing exponential generators, sine wave generators, parabolic generators, etc. Such circuits might utilize the address inputs as part of the mathematical function or not, depending on the desired application.

The outputs of the memories 606a, 606b, rectangle registers 607, and shape logic circuits 605a. 605b pass to the shape multiplexer 608, which is controlled by the SHAPE input. This input is configured to select the desired waveform for a given phase, and is typically held constant for the entire phase. By setting SHAPE to the binary code 0111, for example, the waveform generated will use the template contained in Memory 2 606b. This embodiment shows a data bus width of 8 bits as the output of the shape multiplexor, though more or fewer bits may be used to achieve the shape fidelity required for the therapeutic application.

The output of the shape multiplexer 608 passes into the carry multiplexer 609, which is controlled by the carry output from the sum (Σ) block 602. The carry multiplexer 609 sets the output of the waveform generator to zero when the sum overflows its 24 bits, for example.

Finally, the output of the carry multiplexer 609 drives a digital-to-analog converter 610 (DAC), which emits the normalized waveform output 611 from the Waveform Generator.

It can be seen that with each clock cycle, the sum, and hence the address, is incremented by the amount "STEP". Hence, "STEP" is called the "step size" and sets the rate at which elements of the wave shape template are used to create the waveform. It also implicitly sets the pulse width, since after enough steps of that size, the sum operation will generate a carry, which signals that the waveform generation is complete for the current phase.

The waveform generator constructs stimulation pulses via control from a microcontroller and/or state machine (e.g., a sequencer) that programs the desired shape, step size, and offset required for each phase of the pulse. The microcontroller and/or state machine also control the delays between pulse phases and provide the clock source to the waveform generator.

When memory devices are to be used for waveform generation using stored shape templates, it is often desirable to ensure that a particular point in the template is reached, such as guaranteeing that the peak point of a sine wave is emitted, for example. If the sum were to always start at zero, this may not be possible for some step sizes on some shape samples as the peak could be bypassed in some of those cases. By configuring the OFFSET input appropriately, one can ensure that any selected single sample in the template waveform will be emitted in the synthesized waveform by shifting the chosen samples of the waveform. Thus, depending on the type of waveform, or the scaling of a particular waveform, or both, an appropriate OFFSET value is calculated by the microcontroller for each phase to ensure that the desired particular point in each phase is provided in the output waveform.

Similarly, the same issue can be addressed when using the shape logic, where the OFFSET feature solves the problem in the same way. For example, if the shape logic implements a sine or exponential function, the OFFSET feature could be used to adjust for the peaks.

Figure 7:
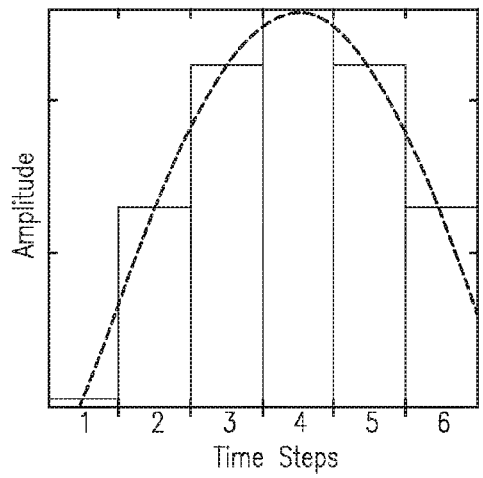
FIG. 7 is an example output waveform construction result of an example waveform generation circuit.

As a possible example of the operation of the example waveform generator of FIG. 6, consider the generation of a six-sample half-sine-wave pulse. Assume the waveform memory is configured with a template waveform of a half sine wave pulse, a portion of the data for an example sampled waveform which is shown in TABLE 1. Further suppose the STEP is set to $2AAAAB and the OFFSET is set to $00. When the waveform generator is started, the phase accumulator will take the values, in successive cycles, $000000, $2AAAAB, $555556, $800001, $AAAAAC, and $D55557 before the sum overflows 24 bits and the waveform stops. The top eight bits of these values are taken to compute the sequence $00, $2A, $55, $80, $AA, $D5, which becomes the addresses into the shape memory. The memory then reads out the values $02, $7F, $DD, $FF, $DD, $7F. FIG. 7 shows these values as the bars, demonstrating the example waveform, while the dashed line illustrates the continuous-time half-sine pulse that these data points approximate. Although the data points are numerically correct, in that they do lie on the sine waveform, there is an asymmetry posed by the first chosen sample amplitude being $02 without a corresponding sample of $02 at the finish, thereby skewing the sine wave to the right. Thus, the overall shape of the pulse might not have the desired fidelity to a sine wave.

Figure 8:
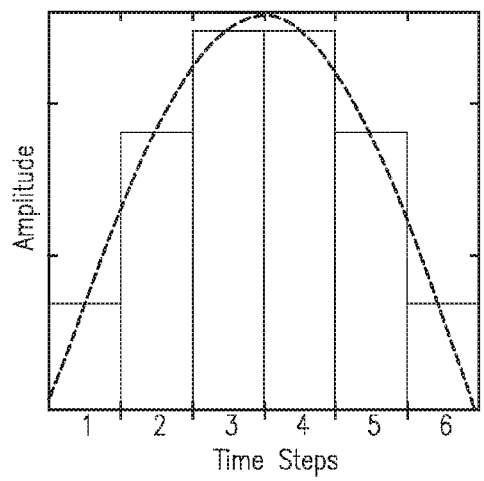
FIG. 8 is another example output waveform construction result of an example waveform generation circuit.

This asymmetry can be corrected by using an appropriate OFFSET input. Again consider the generation of a six-step half-sine-wave pulse, with the waveform memory configured with the data shown in TABLE 1 and the STEP set to $2AAAAB. This time, however, suppose the OFFSET is set to $15, Now, when the waveform generator is started, the phase accumulator will take the values, in successive cycles, $150000, $3FAAAB, $6A5556, $950001, $BFAAAC, and $EA5557, which will result in the sequence of truncated addresses $15, $3F, $6A, $95, $BF, $EA. For these addresses, the shape memory returns the data sequence $43, $B3, $F6, $F6, $B5, $43. FIG. 8 shows these data points as bars, with the continuous-time half sine wave pulse approximated by these pulses drawn as a dashed line. It can easily be seen that the data points both fit the sine wave curve well and have good symmetry. Thus, the OFFSET input can be used as illustrated to adjust the shape of the output waveform.

Figure 9:
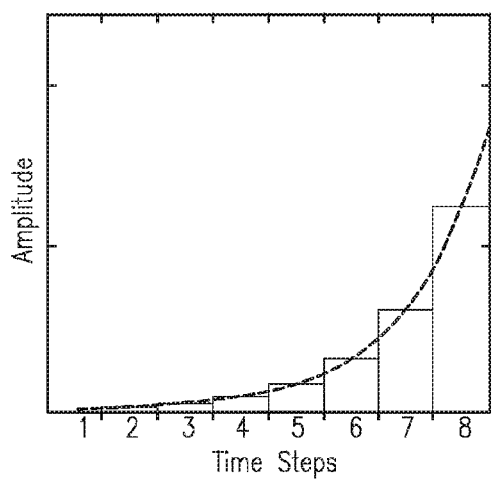
FIG. 9 is another example output waveform construction result of the example waveform generation circuit.

As a second example, consider the creation of an eight-sample rising exponential pulse. The data loaded into the memory for an example of such a sampled waveform are shown in part in TABLE 2. The STEP input is set to $200000 and the OFFSET to $00. The phase accumulator values are the sequence $000000, $200000, $400000, $600000, $800000, $A00000, $000000, $E00000, and the addresses are $00, $20, $40, $60, $80, $A0, $00, $E0. The resulting data sequence is $01, $02, $04, $08, $10, $20, $41, $82. These data are plotted as the bars in FIG. 9, with the continuous-time exponential pulse these points approximate drawn as a dashed line. Although the data fit the ideal exponential pulse, they never reach the maximum amplitude of $FF, which may be considered undesirable. In this situation, an OFFSET may be desirable.

TABLE 1

| Address | Data |
| --- | --- |
| 00 | 02 |
| 01 | 05 |
| 02 | 08 |
| 03 | 0B |
| ... | ... |
| 15 | 43 |
| ... | ... |
| 2A | 7F |
| ... | ... |
| 3F | B3 |
| ... | ... |
| 55 | DD |
| ... | ... |
| 6A | F6 |
| ... | ... |
| 80 | FF |
| ... | ... |
| 95 | F6 |
| ... | ... |
| AA | DD |
| ... | ... |
| BF | B5 |
| ... | ... |
| D5 | 7F |
| ... | ... |
| EA | 43 |
| ... | ... |
| FF | 02 |

TABLE 2

| Address | Data |
| --- | --- |
| 00 | 01 |
| 01 | 01 |
| 02 | 01 |
| 03 | 01 |
| ... | ... |
| 1F | 02 |
| 20 | 02 |
| ... | ... |
| ... | ... |
| 3F | 04 |
| 40 | 04 |
| ... | ... |
| 7F | 10 |
| 80 | 10 |
| ... | ... |
| 9F | 20 |
| A0 | 20 |
| ... | ... |
| BF | 3F |
| C0 | 41 |
| ... | ... |
| DF | 7F |
| E0 | 82 |
| ... | ... |
| FF | FF |

Figure 10:
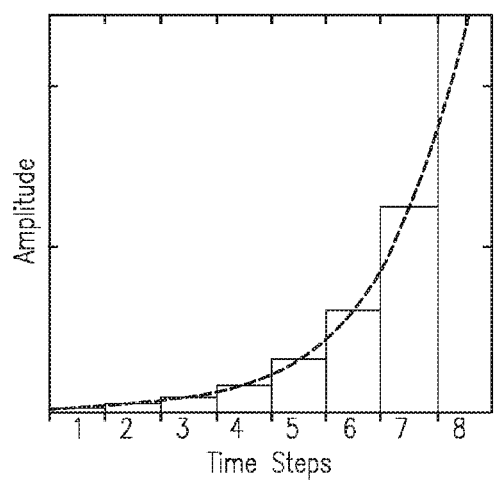
FIG. 10 is another example output waveform construction result of the example waveform generation circuit.

Accordingly, the exponential pulse can be configured to reach its peak value by setting the OFFSET input to $1F. Now, the phase accumulator values are $1F0000, $3F0000, $5F0000, $7F0000, $9F0000, $BF0000, $DF0000, $FF0000, and the resulting addresses are $1F, $3F, $5F, $7F, $9F, $BF, $DF, $FF. The resulting data sequence is $02, $04, $08, $10, $20, $3F, $7F, $FF. These data are plotted as the bars in FIG. 10, with the continuous-time exponential they approximate plotted as a dashed line. It can be seen that the points fit the continuous-time exponential well, and they reach the maximum amplitude. Thus, the OFFSET input provides sufficient control to ensure that a particular sample in the template waveform—in this case the last and peak sample—is reached when the waveform is generated.

Although both of the previous examples were of waveforms shorter than the template waveform, the waveform generator can also be used to create waveforms that are longer than the template waveform. Consider what happens if the STEP input is $00418A and the OFFSET is $00. The phase accumulator values are $000000, $00418A, $008314, $00C49E, $010628, $0147B2, . . . $FEFCE8, $FF3E72, $FF7FFC, $FFC186. With this STEP size, the waveform generator will make 1000 steps before the accumulator overflows 24 bits and waveform generation stops. These phase accumulator values result in the sequence of addresses $00, $00, $00, $00, $01, $01, $FE, $FF, $FF, $FF. It can be seen that when the STEP input is sufficiently small (less than $010000 in this example), the waveform generator will repeat samples from the template waveform to create a pulse of the desired width by stretching the waveform.

It is worth noting that there are trivial variations on this design that are basically equivalent. For example, the memories could be combined into a single larger memory, using one or more additional address lines to select between multiple wave shape templates. Similarly, enable inputs to the memories, rectangle registers, and/or shape logic could achieve a selection function equivalent to part or all of the shape multiplexer. Thus, there are a number of variations that can be used to implement the features of the waveform generator using different alternatives.

There are also several ways for the waveform generation circuitry components to be realized in hardware. First, it is possible to implement all of this circuitry in a single ASIC, either combined on-chip with the microcontroller or separate from it. Second, it is possible to combine some elements of this circuit on an ASIC with various separate components, for example by building most of the waveform generator in the ASIC and interfacing it to separate memories that are not part of the ASIC. Finally, it is also possible to build the waveform generator using discrete components.

Depending on the complexity of the waveforms to be generated and the therapeutic needs of the application, there are many ways to structure the architecture to achieve the features described above. A low-power microcontroller with dedicated programming stored in ROM could be utilized. Or, rather than using a low-power microcontroller, a device such as a more powerful central processing unit or a digital signal processor with appropriate programming stored in a computer readable medium, such as a memory device, could be used to directly synthesize the waveforms. In addition, field-programmable gate arrays could be programmed as a control source, state machine, and/or waveform generator. In this embodiment the preferred memory type for waveform template storage is RAM, though it could be equally effective to use flash memory, EEPROM, or some other form of ROM memory as is known in the art.

Current Divider

In an example embodiment, the output from the waveform generator is provided to a Current Divider to help provide relatively precise control over the normalized waveform amplitude. The Current Divider performs a division operation for scaling the waveform. As an example, such a scaling factor can scale the waveform by a division factor ranging from 1/1, ½, ⅓, and so on to 1/16.

Figure 11:
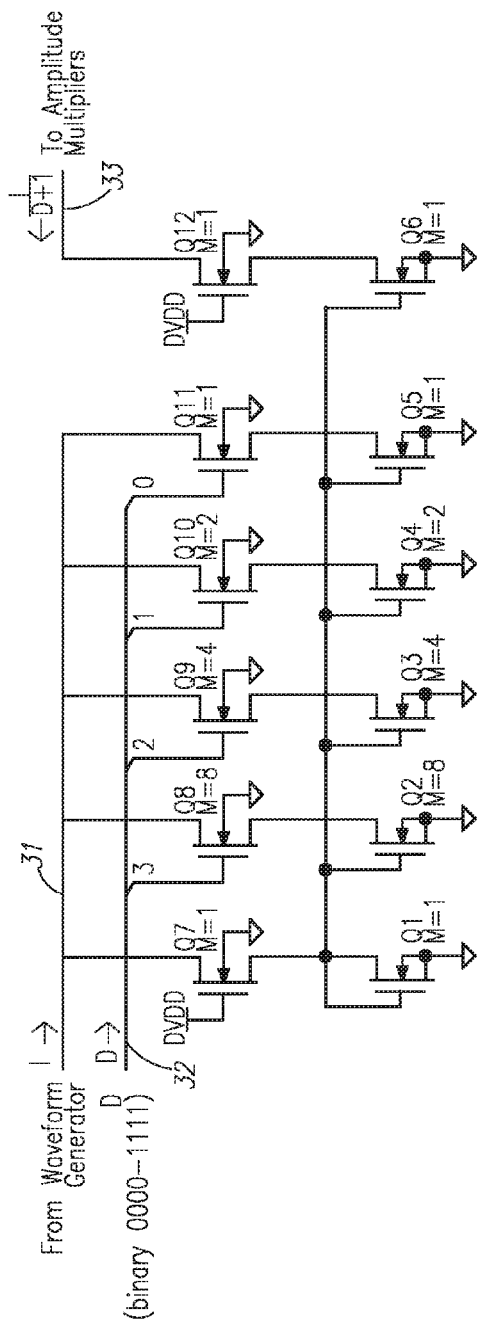
FIG. 11 is a circuit diagram of an example amplitude dividing circuit.

With a current output from the example waveform generator described above, an example current divider can be implemented as shown in FIG. 11. Note that in FIG. 11, the notation "M=n" is used, where n is some number that indicates that the corresponding FET is replicated n times. Each of the n copies of that FET have the same gate, drain, and source connection shown in the diagram.

The circuit in FIG. 11 adapts current mirror techniques to perform current division on the normalized waveform. In the example, a digital 4-bit divisor word enters on the D bus 32, and the analog waveform to be divided enters on the I wire 31. To describe its operation, it is first assumed that all of the FETs in the top row (Q7-Q12) are functioning as switches and all are initially turned "on". A portion of the waveform current coming in the I input 31 passes through FET Q7 and then FET Q1. FET Q1, having its gate tied to its drain, sets the gate voltage for all of the rest of the bottom-row FETs (Q2-Q6) to the value that is needed for it to carry the current flowing through it. Thus, each individual FET in the bottom row is biased to carry the same current value. However, many of the FETs are replicated according to the M factor—for those FETs, each replica is biased to carry that same current. Thus, if all four of Q2-Q5 are carrying current, they will carry a total of 15 (8+4+2+1=15) times the current through Q1, and the current through Q1 will be 1/16 of the current through the I input.

Now, consider the function of the D input 32, which is a 4-bit value controlling Q8-Q11 as switches. When D has the binary value 0000, all four switches (Q8-Q11) are turned off, and the full current of the I input 31 (which is based on the output of the DAC in the Waveform Generator) will flow through Q1. When D has the binary value 0001, Q11 will be turned on, so half the current from I will flow through Q1 and half will flow through Q5. When has the binary value 0100, Q9 will be turned on, enabling the corresponding M=4 FET (Q3). The result is that ⅕ of the input current I will flow through the Q1 and ⅘ will flow through Q3. Thus, the binary value of the input acts as a divisor, controlling how much of the input current I flows through Q1.

The output from the current divider is created by Q6. Its gate voltage is set by Q1, causing the current through it to be the same as that flowing through Q1. Thus, as the D and I inputs are varied, the current sunk at the output is equal to the current sunk by the I input, divided by (D+1), thereby providing a current sink 33 that is a value of I/(D+1)

Q7 and Q12 are configured as switches that are permanently turned on. Their purpose is to match the electrical environment of Q1 and Q6 to that of Q2-Q5, so that all of the bottom-row FETs see similar voltage, resistance, and capacitance in their connected components. This matching improves the accuracy of the division operation.

An alternative implementation could be provided using complimentary circuitry to provide a controlled voltage output when the DAC converter outputs a voltage rather than a current. It is also possible to bypass or eliminate the current divider for applications where its use is not necessary.

Amplitude Multiplier

Figure 19:
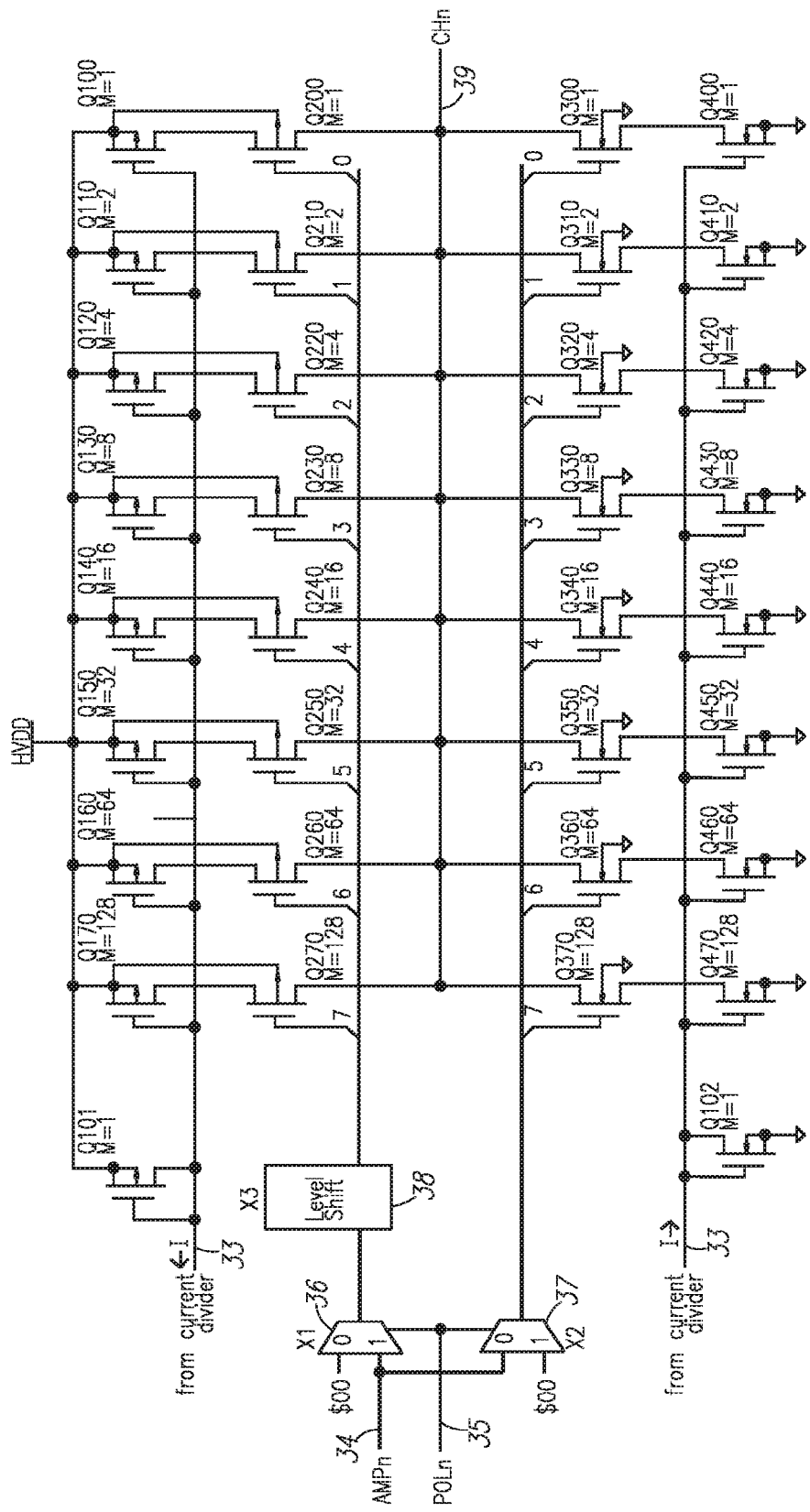
FIG. 19 is a circuit diagram of an example amplitude multiplier circuit.

The output from the waveform generation circuitry is passed to the amplitude multipliers that are associated with corresponding channels. The output from the waveform generation circuitry is replicated in a current mirror, creating one copy of the current per amplitude multiplier. Those copies of the current are passed to the amplitude multipliers that are associated with corresponding channels. Each amplitude multiplier is comprised of two sets of switched current mirrors, one using p-channel FETs (pFETs) and one using n-channel FETs (nFETs). A schematic of one amplitude multiplier (for a single one of the channels) is shown in FIG. 19. The PG contains multiple amplitude multipliers, one for each stimulation channel. In this diagram, the notation "M=n" is again used, where n is some number that indicates that the corresponding FET on the diagram is replicated n times in practice.

To understand the amplitude multiplier, first consider just the pFET side, FETs Q100~Q270 in FIG. 19. The top row, FETs Q100~Q170, forms a current mirror that multiplies the current from FET Q101, which is driven by the current divider output 33. The gate voltage developed by FET Q101 then controls the current through the replicated FETs Q100~Q170. Thus, FETs Q170, marked M=128 (and thus representing a FET replicated 128 times), attempts to output 128 times the current through Q101, whereas the FET marked M=64, Q160, attempts to output 64 times the current through Q101, and so on.

The second row of FETs, Q200~Q270, function as switches that controllably connect the FETs of the first row to the output, CHn 39 representing one channel. To determine how much current is to be supplied on CHn, the suitable switches are turned on. For example, a binary code of 1100 0000 on the bus 34 (AMPn) turns on Q270 and Q260, permitting (128+64)=192 times the current through Q101 to flow to the output CHn.

The bottom two rows of nFETs behave similarly. The bottom row of nFETs, Q400~Q470, form a current mirror that multiplies the current from Q102. nFETs Q300~Q370 serve as a set of switches that controllably connect Q400~Q470 to the output CHn 39. As with the pFETs, the binary code controlling the Q300~Q370 switches sets the current that flows to the output CHn.

The binary codes controlling the pFET and nFET switches are developed by the digital logic on the left side of FIG. 129. The AMPn signal 34 is an 8-bit binary bus that sets the multiplication factor, and the POL input 35 sets the polarity. The POL input 35 controls two multiplexers, 36, 37 that switch the AMPn multiplication factor to either the pFET or nFET switches, respectively, and switch $00, meaning all switches open, to the other set of switches. The output from the multiplexer 36 passes through an inverting level-shift operation 38, before connecting to the pFETs Q200~Q270. The output from the multiplexer 37 drives the nFETs Q300~Q370 directly. While this embodiment shows an 8-bit bus for selecting the multiplication factor, any number of bits may be used to achieve the amplitude resolution desired.

Thus, the current from the current divider is multiplied by the AMPn 34 amplitude value and assigned a polarity set by the PUL 35 bit. The resulting current is then output on CHn 39. The CHn output channel 39 is either connected through a detachable lead and an electrode contact to the tissue to be stimulated, or through protection circuitry to the lead and electrode contact, if protection circuitry is utilized.

It should be noted here that variations of the amplitude multiplier circuitry discussed herein may be included to achieve better accuracy or to meet timing or power requirements. This embodiment of the amplitude multiplier is only one of many configurations that can be used to transfer the output of the waveform generator into an output signal that is provided at the desired electrodes.

Clock Divider

The clock divider 43 (see FIGS. 4, 5) uses standard digital logic techniques to perform frequency division on the CLK input 42. The division factor is configurable and must be an integer. That is to say, if the division factor is 3, then the clock divider outputs one clock cycle for every three cycles of the CLK input. If the division factor is 5, the clock divider outputs one clock cycle for every five cycles of the CLK input. Thus, the CLK frequency should be chosen sufficiently high to satisfy the shortest pulse width that would be expected, and must be high enough to consider the maximum number of samples that are to be used in any given pulse width (or "phase" as that term is used below).

Accordingly, with the application of both time dividing and current dividing, the example PG is capable of performing true division on the output current, without being constrained to integer quotients, and to similarly divide the clock signal to cover a longer period of time. (Note that division of a clock signal results in multiplication of time).

Active Charge Balancing

As defined above, a charge-balanced pulse is one in which the net DC current is zero. This is often done using a passive balancing scheme by accumulating a voltage on a DC blocking capacitor during the stimulation phase, then discharging this voltage during a charge recovery (sometimes called "recharge") phase. This is termed "passive recovery", since the capacitor is passively permitted to discharge to its resting value. In these stimulators, the recovery phase is either exponential or a clamped exponential (owing to the nature of capacitor discharge). A controlled-current recovery phase could also be used, which can be used to avoid the long exponential tail required in passive recovery. In these stimulators, the recovery phase is substantially rectangular. However, accuracy limitations (explained below) mean that one must either give up amplitude resolution or make the recovery phase partially passive in order to ensure a net DC current of zero. In contrast, the PG described herein and in related applications is capable of wave shapes for all phases of the pulse, including both the stimulation and recovery phases. To perform this task, a more sophisticated approach to charge balance is provided.

Figure 12:
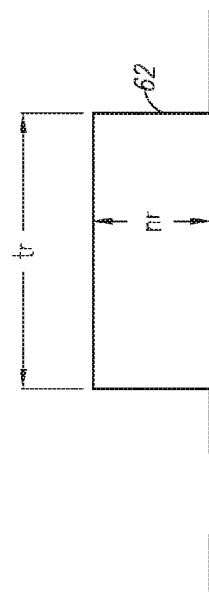
FIG. 12 is a diagram illustrating a two-phase stimulation pulse with charge balancing.

Desired is a means to control the aspect ratio of the charge recovery phase as a function of the amplitude and pulse width of the stimulation phase. Consider FIG. 12, which shows a two-phase stimulation pulse. The first phase 61, the stimulation phase, has a negative polarity, an amplitude of np and a pulse width of tp. The second phase 62, the recovery phase, has a positive polarity, an amplitude of nr and a pulse width of tr. Both amplitudes np and nr have units of digital-to-analog converter (DAC) current or voltage units and are nonnegative integers. Both pulse widths tp and tr have units of clock cycles and are nonnegative integers. The net charge of the pulse is (nr·tr+np·tp). If the aspect ratio of the recovery phase is defined by a scaling factor k, such that the amplitude is scaled by (nr=np/k) and the pulse width is scaled by (tr=k·tp), the charge delivered during the recovery phase is equal to the charge delivered during the stimulation phase.

Figure 13:
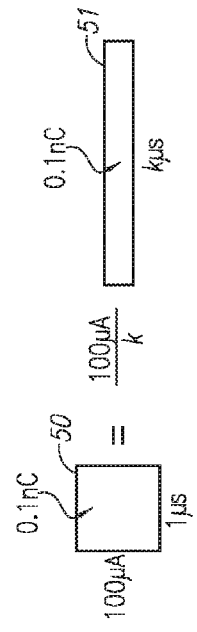
FIG. 13 is another diagram illustrating time scaling.

FIG. 13 illustrates a simple example of how the scaling factor k can be utilized, showing k being used to divide the clock (so that only every k clock cycles are utilized) thereby stretching the wave in time, and a divisor k in amplitude, thereby preserving the overall areas of the waveform pulse 1 50 and pulse 2 51. Such a division results in the same amount of charge transferred by each of the two curves, as their areas are basically equal, but because their polarity is opposite, the charges cancel out. Thus, FIG. 13 shows how a pulse can be modified while preserving the charge using these scaling operations.

Figure 14:
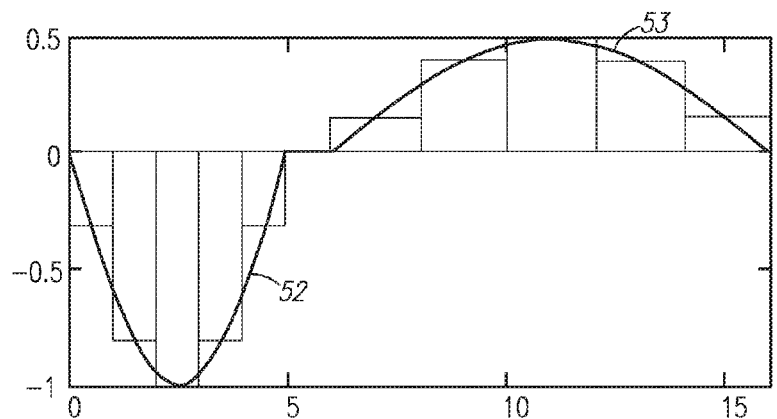
FIG. 14 is an example output waveform construction result of the example waveform generation circuit using scaling features.

FIG. 14 shows this feature being applied to a half-sine wave shape. In this figure, both the stimulation 52 and charge recovery 53 phases are half-sine-waves using five samples each based on the same sample stored in memory.

The recovery phase is scaled by two (k=2) using that value as both the current and clock dividers. Thus, the recovery phase has half the amplitude and twice the duration of the stimulation phase, the net DC charge is zero, and the pulse is charge-balanced, except for possible effects of residual inaccuracies in the system. Because the division is done in analog instead of by changing the amplitude multiplier DAC values, the relationship is truly independent of the amplitude value chosen.

Some residual inaccuracies in the pulse generator circuitry may cause the pulse to have a slightly non-zero net DC current. If this residual current is unacceptable, a solution is to include DC blocking capacitors and passive recovery switches that connect all of the stimulation outputs to a common point, restoring charge balance, as is shown in FIG. 5.

Furthermore, when a pulse consists of phases of different shapes, it may not be possible to generate a completely charge-balanced waveform while maintaining the intended shapes. In such situations, the DC blocking capacitors and passive recovery switches may be used to add a passive charge recovery phase to remove any residual charge.

Accordingly, by utilizing the time clock and current division functions, such balancing operations and scaling of waveform shapes is accommodated.

Arbitrary Waveform Creation

The hardware discussed above is primarily intended to be utilized to generate a waveform of an arbitrary shape to be used for such purposes as spinal stimulation, such as for pain control, for example, for implementation in systems such as those described in FIGS. 1-3. Some examples of waveforms that can be generated by this arrangement are described below, although it must be emphasized that one of the primary benefits of this approach is that waveforms of almost any desired arbitrary shape (scaled in amplitude and time) can be provided using these techniques.

By adding further modifications to the example embodiments, even more flexibility in generating waveform shapes can be provided. For example, utilizing the entire address bus (or even increasing its size) to address much more memory to access many different waveform samples could be utilized. Additional RECT registers can be added to increase the options for rectangular pulses, and/or any number of shape logic circuits could be utilized to provide complex mathematical shapes. As discussed above, the waveform generation circuitry could be replicated to provide additional flexibility in generating output waveforms to the electrodes. Thus, these concepts offer nearly infinite possibilities in generating waveform shapes, as desired, by providing the appropriate adaptations.

Figure 15:
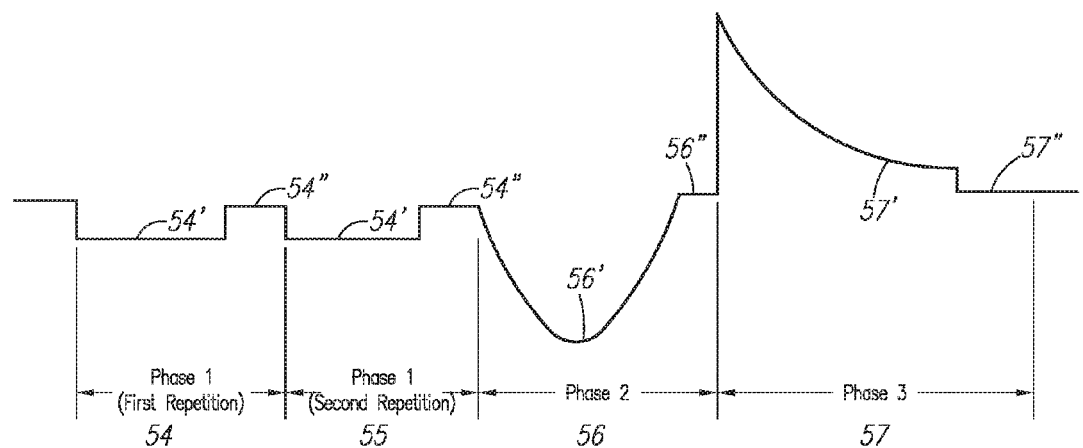
FIG. 15 is an example complex output waveform construction result of the example waveform generation circuit.

As an example of the flexibility of waveform generation, a pulse using these techniques can be divided into two or more phases of stimulation, an example of which is illustrated in FIG. 15, where three different phases are shown, one used twice. For any given channel, each phase has a single polarity and amplitude defined. Each phase has associated with it a clock divider value, a current divider value, a repetition count, a delay value, a waveform step size, a waveform offset value, and a waveform shape. Before generating a pulse, the external microcontroller loads registers in the stimulation ASIC with values representing the phases of the pulse.

To generate the example waveform of FIG. 15, when the microcontroller commands the ASIC to start the pulse, the ASIC then generates the phases in sequence. As each phase begins, the amplitude multipliers are loaded with the amplitude values and the polarities of each channel. The waveform generator is configured for the selected waveform for the phase, the current divider is loaded with the current division factor for the phase, and the clock divider is loaded with the clock division factor for the phase. The waveform generator then generates the waveform for the phase, after which the ASIC inserts a pre-programmed delay before starting the next phase. Phases can be repeated if the phase repetition count is set to a value greater than zero. Once the repetitions, if any, are completed, the ASIC then proceeds to generate the next phase of the pulse.

Thus, in the example of FIG. 15, a first phase 1 54 is generated consisting of a rectangular pulse 54' and a delay 54", a repeat of phase 1 55, a phase 2 56 consisting of a half-sine pulse 56' and a delay 56", and phase 3 pulse 57 consisting of a dying exponential curve 57' and a delay 57".

Figure 18:
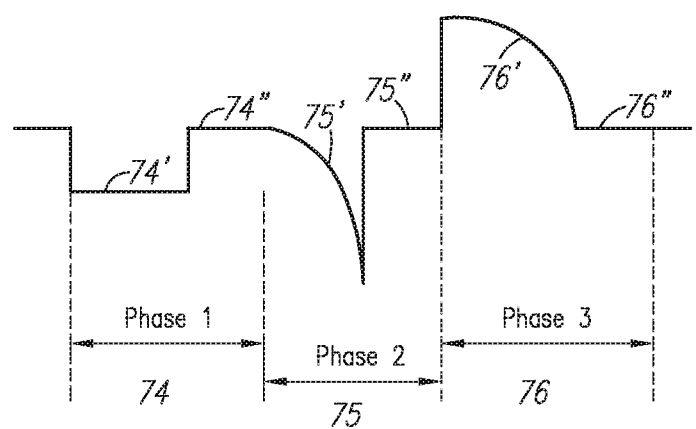
FIG. 18 is another example complex output waveform construction result of the example waveform generation circuit.

In the additional example of FIG. 18, another waveform is generated including a first phase 1 74 consisting of a rectangular pulse 74' with negative polarity and a delay 74", a phase 2 75 consisting of a rising exponential pulse 75' with negative polarity and a delay 75", and phase 3 76 consisting of a quarter-sine pulse 76' with positive polarity and a delay 76".

By the above example architectures, the rectangular pulse could be generated using a RECT register, while the dying exponential, rising exponential, half-sine and quarter-sine pulses could be generated either by sampling respective normalized sine and exponential curves stored in memories, or by using a sine or exponential generator shape logic function, or some combination thereof.

At the microcontroller's command, charge balancing may be achieved by closing the switches that connect all of the DC blocking capacitors (if present) to a common node to passively balance the charge, or by generating an inverse of the curve of FIG. 15 (or a new curve of equal but inverse area) to actively balance the charge, or some combination of the two or by using the scaling procedure discussed above on the curve but changing its scale at an equal inverse charge. It is also possible for charge balance to be achieved in a non-passive manner. Note that because phases 1 and 2 of FIG. 15 are negative pulses, but phase 3 is a positive pulse, by ensuring that the area of phase three is equal to the sum of the areas of phase 1 times 2 plus phase 2 (or adding an additional phase to counter any residual charge), active charge balancing is possible for at least some circumstances. It is also possible to use a combination of active and passive charge balancing.

Figure 16:
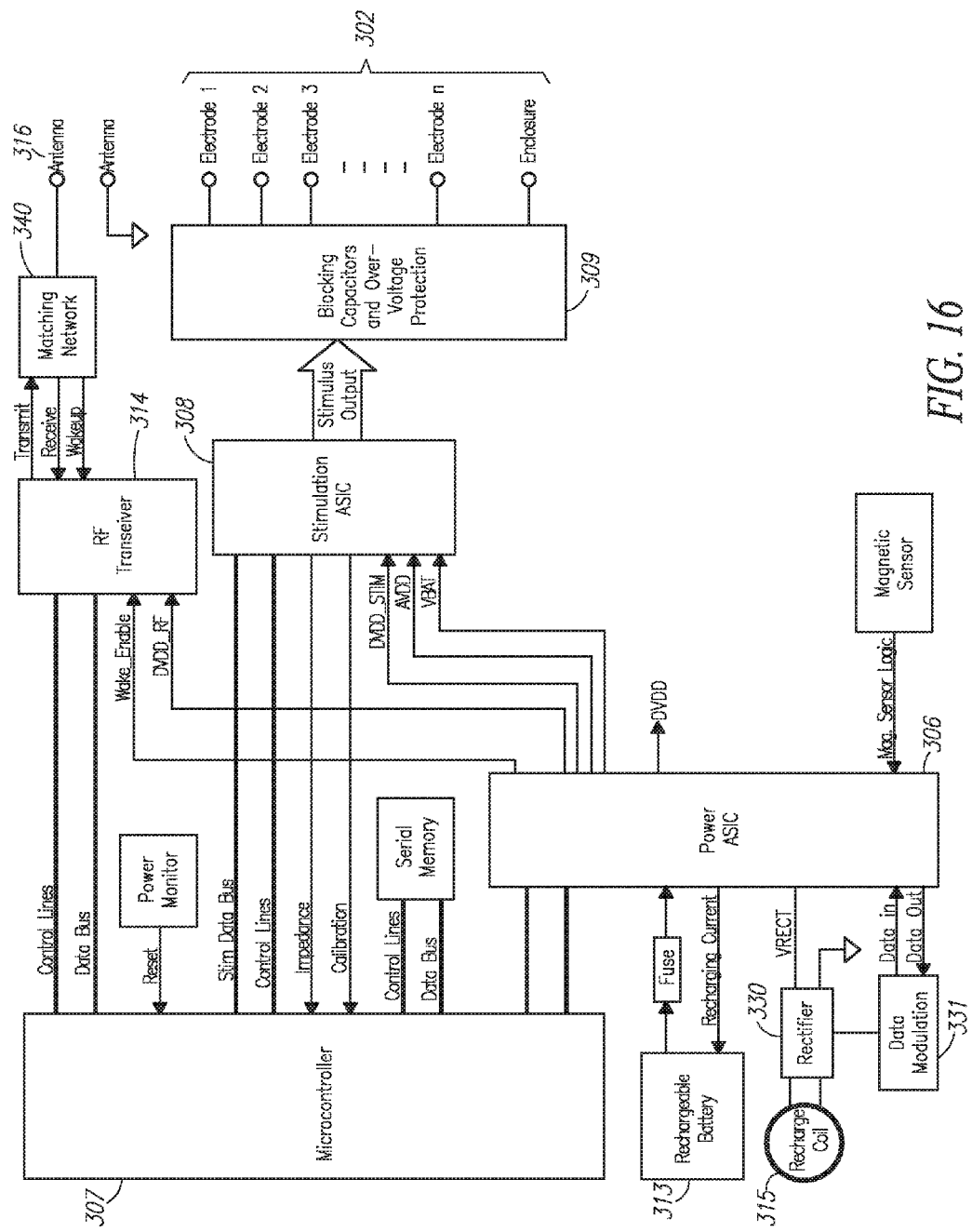
FIG. 16 is a diagram illustrating an example implantable pulse generation device.

FIG. 16 shows an example IPG implementation useful for spinal pain management using an implanted PG that can utilize the features described above in more detail.

The microcontroller 307 will run the software and control the IPG's output. The microcontroller 307 will interface to other functional blocks to monitor IPG status, to send and receive communications, and to drive the channel configuration and output waveforms.

The RF transceiver 314 and matching network 340 and antenna 316 will provide a wireless communications interface to several external devices. The transceiver 314 will send and receive data while automatically handling data flow, RF channel control, error correction, and wakeup detection. The matching network 340 will provide the interface to the IPG's antenna 316, which will be located in the header of the device.

The power architecture consists of the rechargeable battery 313, the Power ASIC 306, recharge coil 315, along with a rectifier 330 and data modulation circuitry 331. The rechargeable battery 313 will provide raw power to the IPG. The recharge coil 315 and rectifier 330 will accept power from a transcutaneous power link and convert it to a DC voltage, while the data modulation circuit 331 will use this link to transfer data to and from the external charger. The Power ASIC 306 will provide control of the recharge process, battery protection, and power for the digital, analog, and high-voltage components of the system.

The Stimulation ASIC 308 will produce the waveforms for stimulation, for example using one of the techniques identified hereinabove. It will provide pulse shaping in arbitrary waveforms to allow complete control of nerve fiber recruitment.

The protection circuitry 309 will enhance safety for both the patient and the IPG itself. The protection circuitry 309 will include protection from electrostatic discharge (ESD) and over-voltage conditions (from defibrillation pulses and electrocautery). The protection circuitry 309 will also include EMI filters. Ultimately, the pulses are delivered to the desired site within the patient by a series of electrodes 302.

Thus, active charge balancing can utilize the same or completely different arbitrary waveforms generated by the PG, reducing or eliminating the need for passive charge balancing using capacitors. For example, the controller could easily initiate an active charge balancing procedure by repeating any given stimulation waveform in a scaled inverse manner for any given electrode, which should substantially balance the charge.

Figure 17:
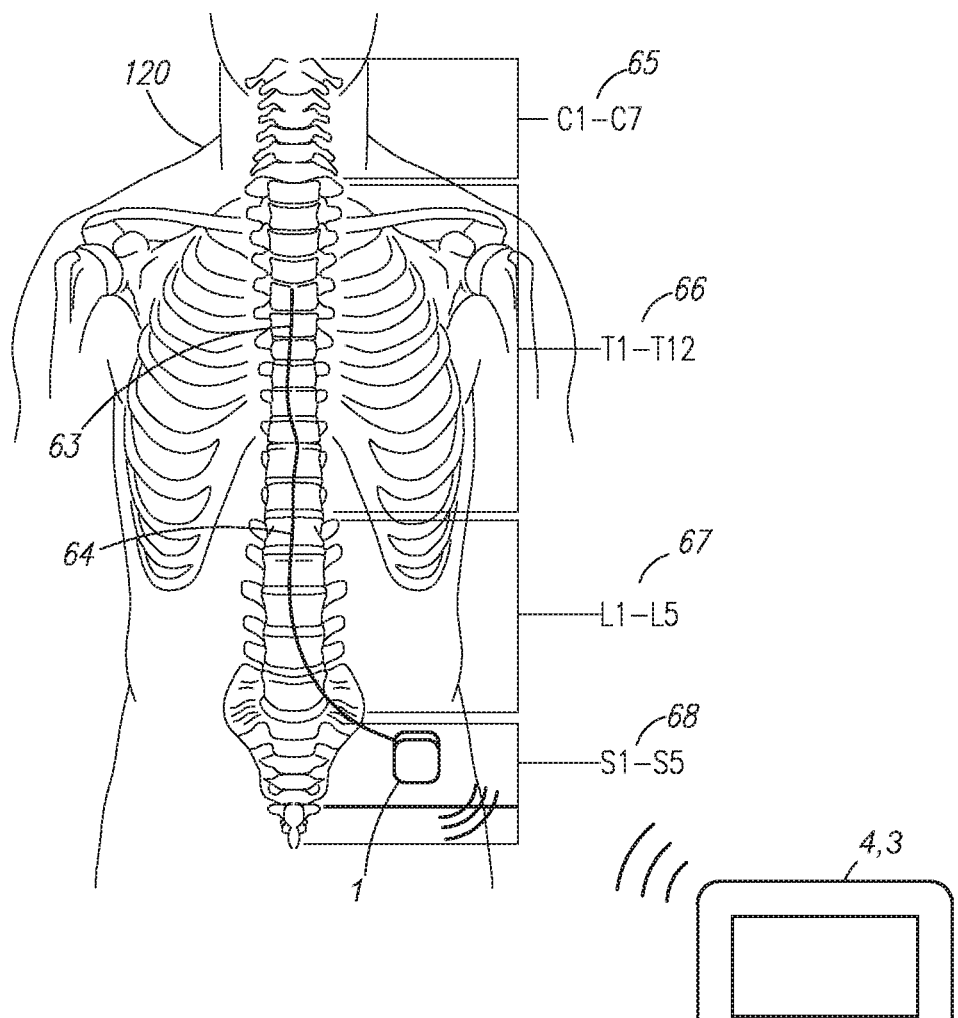
FIG. 17 is a diagram illustrating a medical application of some of the example devices.

FIG. 17 shows an example application of the stimulator system for providing spinal stimulation. In that figure, the IPG 1 (or 101) is shown implanted in a patient. Also shown is the human spine comprising the C1-C7 cervical vertebrae 65, the T1-T12 thoracic vertebrae 66, the L1-L5 lumbar vertebrae 67, and the S1-S6 S5 sacral vertebrae 68. Electrodes 63 are shown disposed at the distal end of the lead 64, which is routed near and along the spine so that the electrodes 63 are positioned near the thoracic vertebrae 66. The electrodes 63 are attached to the IPG 1 via the lead 64.

The leads and electrodes may be positioned anywhere along the spine to deliver/achieve the intended therapeutic effects of spinal cord electrical stimulation in the desired region of the spine. The distal end of the lead with its accompanying electrodes may be located beneath the dura along the epidural space and adjacent to a desired portion of the spinal cord using well-established and known techniques for implanting and positioning SCS leads and electrodes, and the IPG 61 may be programmed using a clinician programmer, patient programmer, or other type of programming device 3, 4 (or 103, 104), as desired (and further described above).

With respect to the Waveform Generator inside the Stimulation ASIC, the provided reference output to the Amplitude Multipliers could be a current, a voltage, or a digital value; all three forms can be similarly utilized, and thus only the current output embodiments are shown. Similarly, the output from the Current Divider could be a current, a voltage, or a digital value. The output of the Iref generator could be either a current or a voltage, or the Iref generator could be omitted if the Waveform Generator outputs a digital value. Thus, using the techniques described herein modified according to the particular output needs can be used to apply these concepts to a great number of different applications.

Furthermore, the Current Divider could be connected between the Iref and the Waveform Generator, or it could be connected between the Waveform Generator and the Amplitude Multipliers. The Current Divider could also be bypassed or omitted. The outputs from the Amplitude Multipliers could be voltages instead of currents.

The terminology of current "flowing to" and "flowing from", or "sink" and "source", can vary depending on whether one uses the convention of current flowing from positive to negative or from negative to positive. Whichever convention one uses is not important to practicing the invention.

The current divider and waveform multiplier could be built with thermometer encoding instead of binary weighting.

The current divider and waveform multiplier could have built-in fixed scaling factors (×2, ×4, ×½, ×¼, etc.).

The operation of truncating the phase accumulator to generate the address could be replaced by a round-to-nearest or ceiling (round-upwards) operation. If a large memory is available, truncation or rounding could be skipped and the entire phase accumulator used as the address.

Many other example embodiments of the invention can be provided through various combinations of the above described features. Although the invention has been described hereinabove using specific examples and embodiments, it will be understood by those skilled in the art that various alternatives may be used and equivalents may be substituted for elements and/or steps described herein, without necessarily deviating from the intended scope of the invention. Modifications may be necessary to adapt the invention to a particular situation or to particular needs without departing from the intended scope of the invention. It is intended that the invention not be limited to the particular implementations and embodiments described herein, but that the claims be given their broadest reasonable interpretation to cover all novel and non-obvious embodiments, literal or equivalent, disclosed or not, covered thereby.

What is claimed is:
1. A medical waveform generator, comprising:
   a waveform generator configured to generate an output waveform comprised of any of a plurality of differently shaped waveforms;
   a time scaling circuit configured to time scale, by a factor of k, the generator output waveform, wherein k is an integer;
   a current divider configured to scale, by a factor of 1/k, an amplitude of the time scaled generator output waveform for outputting an amplitude scaled output waveform; and
   an amplifier configured to amplify the amplitude scaled output waveform for outputting a stimulation waveform.

2. The medical waveform generator of claim 1, further comprising a controller configured for controlling the waveform generator, the time scaling circuit, the current divider, and the amplifier for generating the stimulation waveform having a desired waveform shape, amplitude, and time scale.

3. The medical waveform generator of claim 1, further comprising:
   a plurality of electrode outputs; and
   a plurality of amplifiers configured to amplify an output of the current divider, each one of said amplifiers being configured to output a stimulation waveform corresponding to a different one of said electrode outputs.

4. The medical waveform generator of claim 3, further comprising a passive discharge circuit connected to each one of the electrode outputs.

5. The medical waveform generator of claim 1, wherein said stimulation waveform is comprised of a plurality of active pulses, wherein at least one of said plurality of active pulses is for canceling a charge generated by one or more others of said plurality of pulses.

6. The medical waveform generator of claim 1, wherein said waveform generator includes at least one digital to analog converter configured for converting a digital representation of the output waveform into the output waveform that is analog.

7. The medical waveform generator of claim 1, wherein said waveform generator includes at least one square wave generator configured to generate one or more of the differently shaped waveforms shaped as square waves, and wherein said waveform generator also includes a plurality of memories, each one of said memories configured to store a waveform template for generating a different one of the differently shaped waveforms not shaped as square waves.

8. The medical waveform generator of claim 1, wherein said waveform generator also includes at least one shape logic generator configured to generate one or more of the differently shaped waveforms shaped according to a mathematical function.

9. The medical waveform generator of claim 1, wherein said waveform generator, said time scaling circuit, and said current divider are comprised in an ASIC.

10. A medical waveform generator comprising:
   a plurality of electrode outputs;
   a waveform generator configured to generate an output waveform comprised of any of a plurality of differently shaped waveforms;
   a time scaling circuit configured to input a signal into the waveform generator for time scaling the generator output waveform, wherein the time scaling circuit includes a clock divider that is coupled between a clock signal and the waveform generator, and wherein the clock divider is configured to perform frequency division on the clock signal by a division factor that is an integer;
   a current divider configured to scale an amplitude of the generator output;
   a plurality of amplifiers, each one of the amplifiers being configured to amplify an output of the current divider for outputting a stimulation waveform corresponding to a different one of the electrode outputs; and
   a controller configured to control the waveform generator, the time scaling circuit, the current divider, and the amplifiers to generate the stimulation waveform having a desired waveform shape, amplitude, and time scale.

11. The medical waveform generator of claim 10, further comprising a passive discharge circuit connected to each one of the electrode outputs.

12. The medical waveform generator of claim 10, wherein said stimulation waveform is comprised of a plurality of active pulses, wherein at least one of said plurality of active pulses is for canceling a charge generated by one or more others of said plurality of pulses.

13. The medical waveform generator of claim 10, wherein said waveform generator includes at least one digital to analog converter configured for converting a digital representation of the output waveform into the output waveform that is analog.

14. The medical waveform generator of claim 10, wherein said waveform generator includes at least one square wave generator configured to generate one or more of the differently shaped waveforms shaped as square waves, and wherein said waveform generator also includes a plurality of memories, each one of said memories configured to store a waveform template for generating a different one of the differently shaped waveforms not shaped as square waves.

15. The medical waveform generator of claim 14, wherein said waveform generator also includes at least one shape logic generator configured to generate one or more of the differently shaped waveforms shaped according to a mathematical function.

16. A medical waveform generator, comprising:
   a waveform generator configured to generate an output waveform that includes a plurality of differently shaped waveforms;
   a time scaling circuit configured to time scale the output waveform by a factor of k, wherein k is integer, thereby producing a time-scaled output waveform;
   a current divider configured to scale an amplitude of the time-scaled output waveform by a factor of 1/k, thereby producing an amplitude-scaled output waveform;
   an amplifier configured to amplify the amplitude-scaled output waveform, thereby producing a stimulation waveform for an electrical stimulation therapy; and
   a micro-controller configured to generate one or more control signals;
   wherein at least one of the waveform generator, the time scaling circuit, the current divider, and the amplifier operates in response to the one or more control signals from the micro-controller.

17. The medical waveform generator of claim 16, further comprising:
   a plurality of electrode outputs;
   a plurality of passive discharge circuits that are each coupled to a respective one of the electrode outputs; and
   a plurality of amplifiers that includes the amplifier, wherein each amplifier of the plurality of amplifiers is configured to output a respective stimulation waveform corresponding to a different one of the electrode outputs.

18. The medical waveform generator of claim 16, wherein the stimulation waveform includes a stimulation phase and a recovery phase, and wherein a charge of the stimulation phase is equivalent but inverse to a charge of the recovery phase.

19. The medical waveform generator of claim 16, further comprising a digital-to-analog converter configured for convert a digital representation of a waveform into an analog waveform.

20. The medical waveform generator of claim 16, further comprising:
   a square wave generator configured to generate first members of the differently shaped waveforms shaped as square waves, and
   a plurality of memories, each one of said memories configured to store a waveform template for generating second members of the differently shaped waveforms not shaped as square waves.

* * * * *